(12) United States Patent
Daniel et al.

(10) Patent No.: US 7,223,264 B2
(45) Date of Patent: *May 29, 2007

(54) THERMAL COAGULATION OF TISSUE DURING TISSUE RESECTION

(75) Inventors: Steven A. Daniel, Fremont, CA (US); David L. Morris, Lugarno (AU)

(73) Assignee: Resect Medical, Inc., Fremont, CA (US)

( * ) Notice: Subject to any disclaimer, the term of this patent is extended or adjusted under 35 U.S.C. 154(b) by 387 days.

This patent is subject to a terminal disclaimer.

(21) Appl. No.: 10/800,451

(22) Filed: Mar. 15, 2004

(65) Prior Publication Data

US 2005/0004567 A1    Jan. 6, 2005

Related U.S. Application Data

(63) Continuation-in-part of application No. PCT/US03/21766, filed on Jul. 11, 2003, and a continuation-in-part of application No. 10/413,112, filed on Apr. 14, 2003, now Pat. No. 7,008,421.

(60) Provisional application No. 60/405,051, filed on Aug. 21, 2002.

(51) Int. Cl.
*A61B 18/18* (2006.01)

(52) U.S. Cl. ......................... 606/41; 607/101

(58) Field of Classification Search ............ 606/41, 606/42, 45–50; 607/101–102
See application file for complete search history.

(56) References Cited

U.S. PATENT DOCUMENTS

| | | |
|---|---|---|
| 3,991,770 A | 11/1976 | LeVeen |
| 4,154,246 A | 5/1979 | LeVeen |
| 4,411,266 A | 10/1983 | Cosman |
| 5,231,995 A | 8/1993 | Desai |
| 5,246,438 A | 9/1993 | Langberg |
| 5,366,490 A | 11/1994 | Edwards |
| 5,370,675 A | 12/1994 | Edwards |
| 5,403,311 A | 4/1995 | Abele |
| 5,421,819 A | 6/1995 | Edwards |
| 5,458,597 A | 10/1995 | Edwards |
| 5,470,309 A | 11/1995 | Edwards |
| 5,472,441 A | 12/1995 | Edwards |
| 5,480,397 A | 1/1996 | Eggers |
| 5,484,400 A | 1/1996 | Edwards |
| 5,486,161 A | 1/1996 | Lax |
| 5,531,676 A | 7/1996 | Edwards |

(Continued)

*Primary Examiner*—Michael Peffley
(74) *Attorney, Agent, or Firm*—Courtney Staniford & Gregory LLP

(57) ABSTRACT

Methods for performing coagulation necrosis of biological tissue are provided. The methods include configuring electrode arrays to provide balanced energy density in target tissue volumes using two or more pair of electrodes. The electrode array configuration includes at least one of irregular spacing between one or more pairs of electrodes and one or more electrode diameters. The methods further include deploying each electrode of an array at a selected depth in the target tissue volume in accordance with the configuration. Energy is then delivered to the target tissue volume using power sources coupled to the electrodes. The methods control power delivery in response to at least one of elapsed time of delivery, temperatures of the target tissue volume, and impedance levels in the target tissue volume to provide balanced or uniform energy throughout the target tissue volume. The methods generate planes of coagulated tissue.

36 Claims, 26 Drawing Sheets

U.S. PATENT DOCUMENTS

| | | |
|---|---|---|
| 5,536,267 A | 7/1996 | Edwards |
| 5,542,916 A | 8/1996 | Hirsch |
| 5,556,377 A | 9/1996 | Rosen |
| 5,573,533 A | 11/1996 | Strul |
| 5,599,345 A | 2/1997 | Edwards |
| 5,599,346 A | 2/1997 | Edwards |
| 5,609,151 A | 3/1997 | Mulier |
| 5,672,173 A | 9/1997 | Gough |
| 5,672,174 A | 9/1997 | Gough |
| 5,697,909 A | 12/1997 | Eggers |
| 5,720,719 A | 2/1998 | Edwards |
| 5,722,975 A | 3/1998 | Edwards |
| 5,728,143 A | 3/1998 | Gough |
| 5,735,847 A | 4/1998 | Gough |
| 5,782,827 A | 7/1998 | Gough |
| 5,800,484 A | 9/1998 | Gough |
| 5,810,804 A | 9/1998 | Gough |
| 5,817,092 A | 10/1998 | Behl |
| 5,827,276 A | 10/1998 | LeVeen |
| 5,855,576 A | 1/1999 | LeVeen |
| 5,863,290 A | 1/1999 | Gough |
| 5,865,788 A | 2/1999 | Edwards |
| 5,868,740 A | 2/1999 | LeVeen |
| 5,913,855 A | 6/1999 | Gough |
| 5,925,042 A | 7/1999 | Gough |
| 5,947,964 A | 9/1999 | Eggers |
| 5,954,717 A | 9/1999 | Behl |
| 5,957,961 A | 9/1999 | Maguire |
| 5,980,517 A | 11/1999 | Gough |
| 5,993,447 A | 11/1999 | Blewett |
| 6,007,499 A | 12/1999 | Martin |
| 6,050,992 A | 4/2000 | Nichols |
| 6,059,780 A | 5/2000 | Gough |
| 6,080,149 A | 6/2000 | Huang |
| 6,090,105 A | 7/2000 | Zepeda |
| 6,212,433 B1 | 4/2001 | Behl |
| 6,235,023 B1 | 5/2001 | Lee |
| 6,241,725 B1 | 6/2001 | Cosman |
| 6,312,426 B1 | 11/2001 | Goldberg |
| 6,312,428 B1 | 11/2001 | Eggers |
| 6,337,998 B1 | 1/2002 | Behl |
| 6,358,246 B1 | 3/2002 | Behl |
| 6,428,538 B1 | 8/2002 | Blewett |
| 6,530,922 B2 | 3/2003 | Cosman |

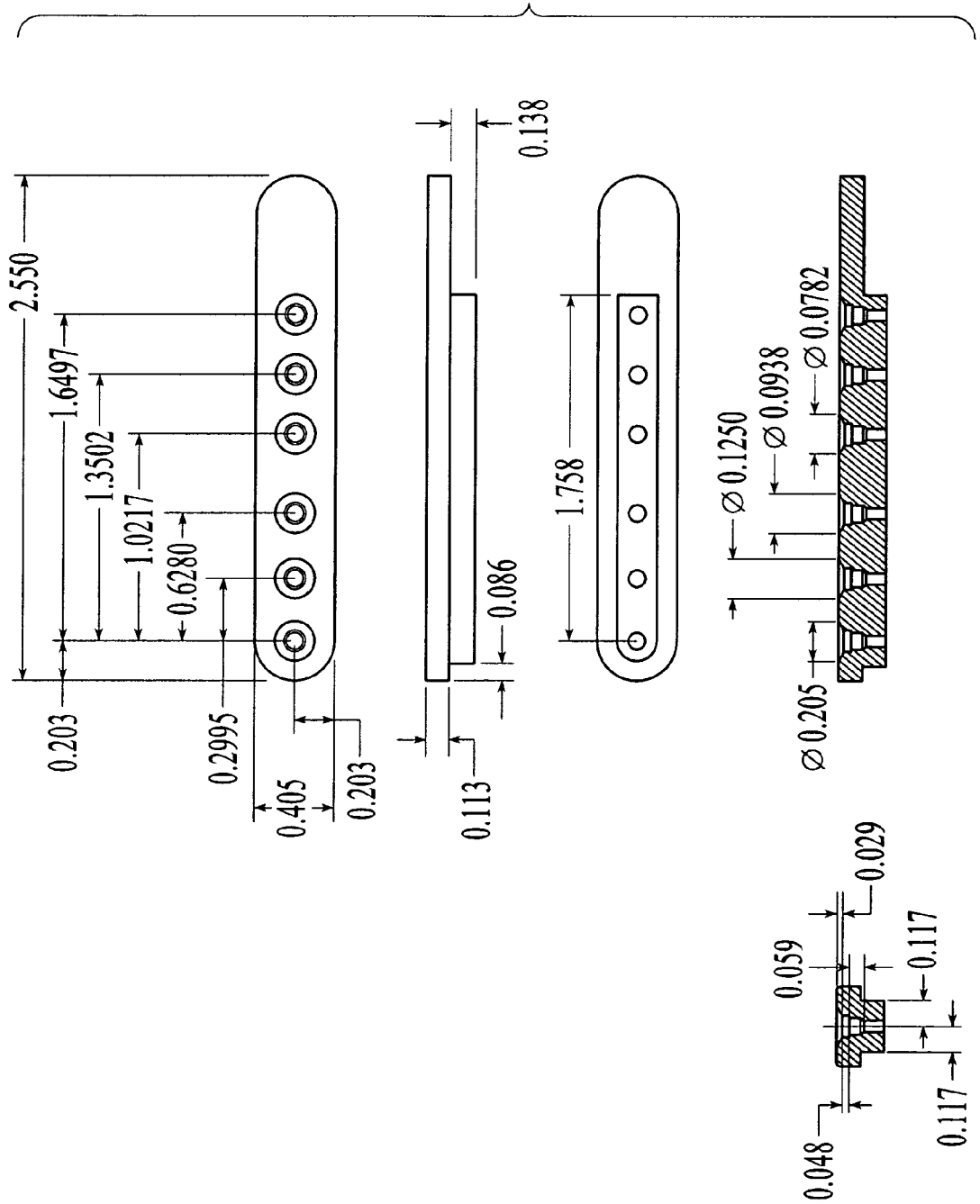

| | Zone 1 | Zone 2 | Zone 3 | Zone 4 | Zone 5 |
|---|---|---|---|---|---|
| 480 — Values with Balanced Circuit | 219.5<br>18.86<br>7.235 | 200.1<br>20.69<br>19.56<br>7.935 | 167<br>24.79<br>24.79<br>23.45<br>9.51 | 200.1<br>20.69<br>19.56<br>7.935 | 219.5<br>18.86<br>7.235 |
| 482 — Total Power per Zone | 245.595 | 248.285 | 249.54 | 248.285 | 245.595 |
| % Error per Zone | 0 | -1.095299 | -1.606303 | -1.095299 | 0 |
| "Spacing" Value per Zone | 12.4 | 13.6 | 16.3 | 13.6 | 12.4 |
| 484 — "Spacing" Ratio per Zone | 1.00 | 1.097 | 1.315 | 1.097 | 1.00 |
| 486 — "Spacing" Ratio per Zone | 0.760736 | 0.834356 | 1 | 0.834356 | 0.760736 4.190184 |

| | 580 ⌒ Values with Balanced Circuit | | | | | | |
|---|---|---|---|---|---|---|---|
| | Zone 1 | Zone 2 | Zone 3 | Zone 4 | Zone 5 | Zone 6 | Zone 7 |
| | 503.1<br>39.96<br>12.71<br>7.097 | 445.6<br>45.11<br>14.36<br>37.91<br>13.78<br>8.013 | 354.5<br>56.71<br>18.05<br>41.24<br>18.05<br>47.65<br>17.33<br>10.07 | 380.4<br>16.82<br>38.43<br>16.82<br>44.41<br>44.41<br>16.15<br>9.387 | 354.5<br>18.05<br>41.24<br>18.05<br>56.71<br>47.65<br>17.33<br>10.07 | 445.6<br>14.36<br>45.11<br>37.91<br>13.78<br>8.013 | 503.1<br>12.71<br>39.96<br>7.097 |
| 582 ⌒ Total Power per Zone | 562.87 | 564.77 | 563.60 | 566.83 | 563.60 | 564.77 | 562.87 |
| % Error per Zone | 0.00 | 0.34 | 0.13 | 0.70 | 0.13 | 0.34 | 0.00 |
| "Spacing" Value per Zone | 31 | 35 | 44 | 41 | 44 | 35 | 31 |
| 584 ⌒ "Spacing" Ratio per Zone | 1.000 | 1.129 | 1.419 | 1.323 | 1.419 | 1.129 | 1.000 |
| 586 ⌒ "Spacing" Ratio per Zone | 0.704545 | 0.795455 | 1 | 0.931818 | 1 | 0.795455 | 0.704545 |

FIG.5C

| R1 | R2 | R3 | R4 | R5 |
|---|---|---|---|---|
| 219.5 mW | 195.7 mW | 174.4 mW | 195.7 mW | 219.4 mW |
| R6 | R7 | R8 | 0 deg | 0 deg |
| 19.21 mW | 21.54 mW | 24.17 mW | R10 | R11 |
| 0 deg | 0 deg | R9 | 21.54 mW | 19.21 mW |
| | | 24.17 mW | | 0 deg |

| | R12 | R13 | R14 | |
|---|---|---|---|---|
| | 20.08 mW | 22.53 mW | 20.08 mW | |
| R15 | R16 | R17 | R18 | R19 |
| 7.235 mW | 8.13 mW | 9.124 mW | 8.13 mW | 7.253 mW |
| 0 deg | 0 deg | 0 deg | 0 deg | 0 deg |
| R1 | R2 | R3 | R4 | R5 |
| 1.649 mV | 1.649 mV | 1.649 mV | 1.649 mV | 1.649 mV |
| 133 mA | 105.7 mA | 105.7 mA | 118.7 mA | 133 mA |
| R6 | R7 | R8 | | |
| 488.1 mV | 547.2 mV | 614.1 mV | | |
| 39.36 mA | 39.36 mA | 39.36 mA | | |
| | | R9 | R10 | R11 |
| | | 614.1 mV | 547.2 mV | 488.1 mV |
| | | 39.36 mA | 39.36 mA | 39.36 mA |
| | R12 | R13 | R14 | |
| | 528.3 mV | 592.9 mV | 528.3 mV | |
| | 38 mA | 38 mA | 38 mA | |
| R15 | R16 | R17 | R18 | R19 |
| 299.9 mV | 336.2 mV | 377.3 mV | 336.2 mV | 299.9 mV |
| 24.18 mA | 24.18 mA | 24.18 mA | 24.18 mA | 24.18 mA |

| 680 ~ Values with Balanced Circuit | | | | | |
|---|---|---|---|---|---|
| | Zone 1 | Zone 2 | Zone 3 | Zone 4 | Zone 5 |
| | 133 | 118.7 | 105.7 | 118.7 | 133 |
| | 39.36 | 39.36 | 39.36 | 39.36 | 39.36 |
| | 24.18 | 38 | 39.36 | 38 | 24.18 |
| | | 24.18 | 38 | 24.18 | |
| | | | 24.18 | | |
| Total Current per Zone | 196.54 | 220.24 | 246.6 | 220.24 | 196.54 |
| "Spacing" Value per Zone | 12.4 | 13.9 | 15.6 | 13.9 | 12.4 |
| 682 ~ Current Density per Zone | 15.85 | 15.8446 | 15.80769 | 15.8446 | 15.85 |
| % Error | 0.0 | 0.0 | 0.3 | 0.0 | 0.0 |
| 684 ~ "Spacing" Ratio per Zone | 1.00 | 1.12 | 1.26 | 1.12 | 1.00 |
| 686 ~ "Spacing" Ratio per Zone | 0.79 | 0.89 | 1.00 | 0.89 | 0.79 |

FIG.6C

THERMAL COAGULATION OF TISSUE DURING TISSUE RESECTION

RELATED APPLICATIONS

This application is a continuation-in-part application of International Application Number PCT/US03/21766, filed Jul. 11, 2003, and a continuation-in-part application of U.S. patent application Ser. No. 10/413,112 now U.S. Pat. No. 7,008,421, filed Apr. 14, 2003, which application claims the benefit of U.S. Patent Application No. 60/405,051, filed Aug. 21, 2002.

TECHNICAL FIELD

This invention relates generally to an apparatus and method that aids in the resection of tissue, and more particularly to the bloodless or near bloodless resection of tissue.

BACKGROUND

Standard surgical procedures for trauma, cancer and transplants in the kidney, liver, and like organs have several key shortcomings affecting efficacy, morbidity and mortality. In an effort to fully remove or resect an organ, the surgeon may be forced to breach the tissue causing a large amount of bleeding. Careful hemostasis can minimize blood loss and complications but is laborious and time consuming using the systems and methods known in the art. Uncontrollable bleeding, for example, is one of the leading causes that prevent such treatments from being offered to patients with cirrhotic livers. In cancer patients, the surgeon must exercise care in an attempt not to allow any tumor cells to remain at a site of resection since any viable tumor cells may cause a recurrence of the cancer and negate the benefit of the procedure. Furthermore, surgeons can reduce the risk of complications by performing these procedures in an expedient manner to minimize anesthesia time and blood loss.

Typical methods for creating resections or controlling bleeding and blood loss include scalpels, electrocautery, ultrasonic scalpels, argon beam coagulators, and radio frequency (RF) surface dissectors. However, these therapies in their present form have several critical drawbacks including: (i) a complete lack or partial inability to create a hemostatic or near-hemostatic resection plane with any significant depth; (ii) a partial or complete lack of ability to make the tissue resection plane unable to support the growth of cancer cells left on the surface; (iii) a partial or complete lack of ability to kill cancerous cells remaining from an in adequate resection margin; (iv) an ability to reduce the operative time and likewise the complications resulting from the prolonged exposure to anesthesia; and (v) an ability to reduce the level of skill required to perform a safe and effective resection thereby allowing a greater availability of the treatment to the patient population.

BRIEF DESCRIPTION OF THE FIGURES

FIG. 2 and FIG. 3 are schematics of the energy director guide, including various views, under an embodiment.

FIG. 4C is a table including power dissipation and spacing information corresponding to an energy director configuration providing balanced energy, under the embodiment of FIG. 4A.

FIG. 5B shows a table including power dissipation values corresponding to an energy director configuration providing balanced energy, under the embodiment of FIG. 5A.

FIG. 5C is a table including power dissipation and spacing information corresponding to an energy director configuration providing balanced energy, under the embodiment of FIG. 5A.

FIG. 6B shows a table including power dissipation information corresponding to an energy director configuration providing balanced energy, under the embodiment of FIG. 6A.

FIG. 6C is a table including current and spacing information corresponding to an energy director configuration providing balanced energy, under the embodiment of FIG. 6A.

Figure 1:
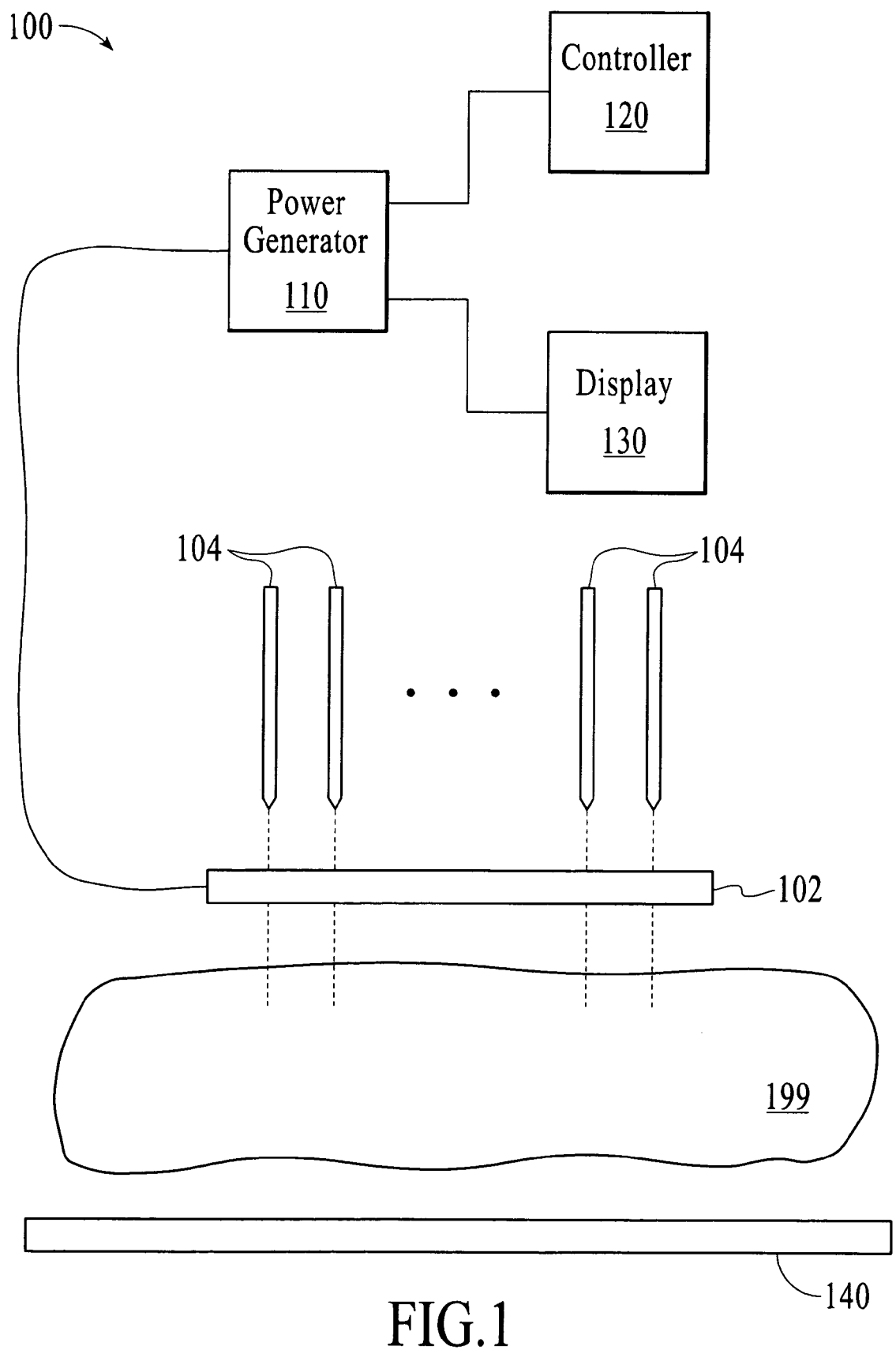
FIG. 1 is a tissue ablation system, under an embodiment.

In the drawings, the same reference numbers identify identical or substantially similar elements or acts. To easily identify the discussion of any particular element or act, the most significant digit or digits in a reference number refer to the Figure number in which that element is first introduced (e.g., element 102 is first introduced and discussed with respect to FIG. 1).

DETAILED DESCRIPTION

A tissue ablation system including numerous components and methods is described in detail herein. The tissue ablation system generates an avascular volume of coagulated tissue that aids in the bloodless or near-bloodless resection of various biological tissues from a variety of organs including, for example, the liver, spleen, kidney, and various other organs of the body. In the following description, numerous specific details are introduced to provide a thorough understanding of, and enabling description for, embodiments of the invention. One skilled in the relevant art, however, will recognize that the invention can be practiced without one or more of the specific details, or with other components, systems, etc. In other instances, well-known structures or operations are not shown, or are not described in detail, to avoid obscuring aspects of the invention.

FIG. 1 is a tissue ablation system 100, under an embodiment. The tissue ablation system 100 includes an energy director guide 102, or guide, and two or more pair 104 of bipolar energy directors, also referred to herein as electrodes. The tissue ablation system 100 is used for the thermal coagulation necrosis of soft tissues as an aid during tissue resection. Alternative embodiments of the tissue ablation system 100 can include monopolar energy directors and various combinations of bipolar and monopolar energy directors. The energy directors 104 are configured for insertion into a volume of biological tissue 199. The energy director guide 102 configures the energy directors to provide approximately uniform power or energy distribution through a tissue volume, referred to as the target tissue or target tissue volume. The target tissue volume includes the volume within an approximately one (1) centimeter (cm) radius around each energy director 104 extending over the conducting length of the energy director 104, but is not so limited. The target tissue volume forms at least one plane of coagulated tissue.

The energy director guide 102 and the energy directors 104 are coupled among at least one generator 110, or power source, but are not so limited. The energy directors 104 of an embodiment couple to the generator 110 via the energy director guide 102. Alternatively, the energy directors 104 can couple directly to the generator 110 via a wire, cable, or other conduit.

Using the bipolar configuration of the energy directors 104, one electrode of an electrode pair serves as a source and the other electrode of the pair serves as a sink for the power received from the generator 110. Therefore, one electrode is disposed at the opposite voltage (pole) to the other so that power from the generator is drawn directly from one electrode to the other. The bipolar electrode arrangement insures more localized and smaller heat ablation volumes, but the embodiment is not so limited.

The alternating polarity series of energy directors includes various series combinations of alternating polarities. For example, in an embodiment using six (6) energy directors, the alternating polarity is: positive polarity (+), negative polarity (−), +, −, +, −. An alternative polarity series is: +, +, −, −, +, +. Another alternative polarity series is: −, −, +, +, −, −. Yet another alternative polarity series is: +, +, +, −, −, −. Still other alternative polarity series can include: +, +, −, +, −, −. These examples are exemplary only, and the tissue ablation system 100 described herein is not limited to six (6) electrodes or to these alternating polarities.

The energy directors 104, while configured appropriately for insertion into particular tissue types, have a shape and a pattern that supports coupling to the target tissue and allows the energy directors 104 to deliver sufficient energy to cause the tissue to become hemostatic, such as by coagulation of the tissue, thereby facilitating resection of a selected tissue volume. The energy directors 104 of an embodiment include rigid shafts that are of sufficient stiffness to be easily urged into the target tissue 199 and coupled to the tissue 199 while retaining their shape.

The energy directors 104 terminate in non- or minimally-traumatic tissue-penetrating tips of various configurations known in the art as appropriate to the tissue type of the target tissue 199. The energy director tip configurations of an embodiment include fully rounded tips, flat tips, blunt tips, and rounded tips, but are not so limited. These configurations facilitate insertion of the energy directors into different types of target tissue while protecting the user from sharp points that, during normal handling, pose a puncture hazard to the user. This is particularly important since the energy directors could be contaminated with potentially deadly material including viruses such as Hepatitis-C and Human Immunodeficiency Virus (HIV) that could be transmitted to the user through a puncture wound.

The energy directors of an embodiment can have many different sizes depending upon the energy delivery parameters (current, impedance, etc.) of the corresponding system. For example, energy director diameters are approximately in the range of 0.015 inches to 0.125 inches, but are not so limited. Energy director lengths are approximately in the range of 4 cm to 10 cm, but are not so limited. Energy directors include materials selected from among conductive or plated plastics, super alloys including shape memory alloys, and stainless steel, to name a few.

Further, an array of energy directors can include energy directors of different sizes and lengths. For example, an energy director array of an embodiment includes six (6) energy directors in a linear array, where the energy director on each end of the array is a 16-gage electrode while the four (4) energy directors that form the center of the array are 15-gage electrodes. The use of energy directors having different diameters allows for balancing of energy/energy density in the target tissue by, for example, decreasing the total energy dissipation in the target tissue at the ends of the array (smaller energy directors) and thereby limiting/controlling the effect (necrosis) on the tissue beyond the ends of the energy director array. Therefore, the use of energy directors having different diameters provides an additional means of control over energy balancing in the target tissue in addition to the spacing between the energy directors.

The energy directors 104 of various alternative embodiments can include materials that support bending and/or shaping of the energy directors 104. Further, the energy directors 104 of alternative embodiments can include non-conducting materials, coatings, and/or coverings in various segments and/or proportions along the shaft of the energy director 104 as appropriate to the energy delivery requirements of the corresponding procedure and/or the type of target tissue.

The generator 110 of an embodiment delivers pre-specified amounts of energy at selectable frequencies in order to coagulate and/or cut tissue, but is not so limited. The generator 110 of an embodiment is an RF generator that supports output power in the range of approximately zero to 200 Watts, output current in the range of approximately 0.1 amps to four (4) amps, and output impedances generally in the range of approximately two (2) to 150 Ohms, across a frequency range of approximately 1 kHz to 1 MHz, but is not so limited.

It is understood that variations in the choice of electrical output parameters from the generator to monitor or control the tissue ablation process may vary widely depending on tissue type, operator experience, technique, and/or preference. For example, in one embodiment a common voltage is applied to all the energy directors of an array simultaneously. As an alternative embodiment, the operator may choose to control the current to the individual energy directors of the array or the total current of the array as a whole.

Further, voltage variations on each energy director can be applied to achieve constant current output from each energy director. Alternatively, constant power output from each energy director may be sought in some procedures. Additionally, voltage variations or phase differences between energy directors can be implemented to achieve pre-specified temperature distributions in the tissue as monitored by temperature sensors in the tissue or by visualization of temperature distribution using techniques known in the art. Accordingly, the choice of electrical output type, sequence, and levels and the distribution to the energy directors of the array should be considered to have wide variations within the scope of this invention.

Various geometric factors relating to the target tissue also affect the heating of tissue during ablation. These include the tissue edges as well as the ablation surface volume. As the amount of ablative surface area increases, the heat loss also increases. Ablation edges, sides, and ends all can have an effect on the heat loss during ablation.

The ablation system of an embodiment ablates the target tissue by heating the tissue uniformly between the energy directors. In order to accomplish the uniform heating, the current density in the tissue immediately surrounding the energy conduit should not be significantly greater than the current density in the tissue between the energy conduits. As an example, consider the case where the size of the electrode is relatively small so that the tissue/energy conduit contact area is small. This results in a high currently density around the energy conduit leading to dominant heating in the immediate vicinity of the electrodes, increasing the probability of unwanted tissue charring and ultimately limiting the amount of energy that can be delivered to the tissue. Methods provided herein to address this include using a larger tissue/energy conduit contact area, cooling the electrode, and introducing a more conductive material around the electrode area, for example hypertonic saline.

The tissue ablation system 100 can include any number of additional components like, for example, a controller 120 to semi-automatically or automatically control delivery of energy from the generator. The controller can, for example, increase the power output to the electrodes, control temperature when the energy directors include temperature sensors or when receiving temperature information from remote sensors, and/or monitor or control impedance, power, current, voltage, and/or other output parameters. The functions of the controller 120 can be integrated with those of the generator 110, can be integrated with other components of the tissue ablation system 100, or can be in the form of stand-alone units coupled among components of the tissue ablation system 100, but are not so limited.

Moreover, the tissue ablation system 100 can include a display 130 that provides a display of heating parameters such as temperature for one or more of the energy directors, impedance, power, current, timing information, and/or voltage of the generator output. The functions of the display 130 can be integrated with those of the generator 110, can be integrated with other components of the tissue ablation system 100, or can be in the form of stand-alone units coupled among components of the tissue ablation system 100, but are not so limited.

Various alternative embodiments of the tissue ablation system 200 can also include a biocompatible thermal shield 140. The thermal shield 140 serves to protect the organs and tissue that surround the target biological tissue 199 from the effects of the procedures described herein associated with treatment using the tissue ablation system 200.

Placement of the energy directors described herein controls the distribution of energy imparted to the target tissue. As such, the energy director configurations described herein support approximately uniform energy distribution and/or current density, and thus more uniform temperatures, through the target tissue volume. An example of this includes the use of RF energy where, for a number of energy directors, and as described below, generally uniform energy distribution is obtained using relatively smaller spacing between the energy directors toward the outside of a linear energy director array and relatively larger spacing between the energy directors toward the center of the energy director array. The spacing between the energy directors is established and maintained using the energy director guide, a description of which follows. An example of the tissue ablation system 100 of an embodiment includes the InLine™ Bi-Polar RF Linear Coagulation System available from Resect Medical™ of Fremont, Calif.

Figure 2:
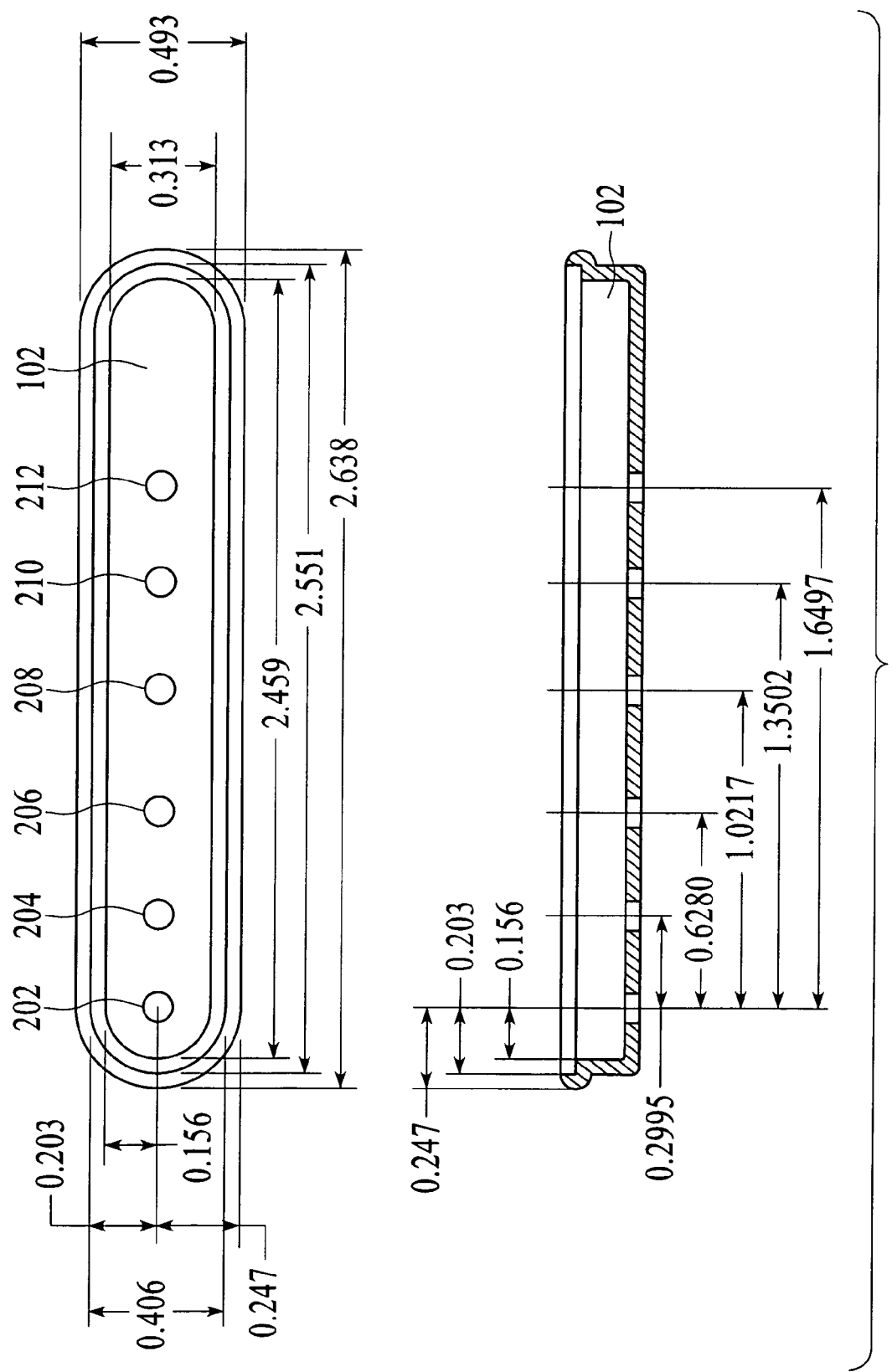

FIGS. 2 and 3 are schematics of an energy director guide 102, including various views, under an embodiment. The dimensions shown are in inches. The energy director guide 102 includes a support body having a linear series of channels 202-212 that receive or carry the energy directors. The support body of an embodiment includes first and second end portions with a surface extending between the first and second end portions. The channels 202-212 can also be referred to as orifices or openings, but are not so limited.

The energy director guide of various alternative embodiments can include a non-linear series of channels, and various combinations of a linear and a non-linear series of channels. The energy directors of an embodiment alternate in polarity or, alternatively, are in groups or sets that alternate in polarity, as described above, but the embodiment is not so limited. The configuration of the channels 202-212 in the guide supports delivery of an energy distribution or radiation pattern in the tissue by the energy directors that provides sufficient and even coagulation in the target tissue volume. Typically an ablation width in the range of approximately 0.5 cm to 1.5 cm is used to facilitate the resection, but the embodiment is not so limited. The energy director guides include biocompatible materials like, for example, non-conductive plastics like polycarbonate plastic, ULTEM® (polyetherimide), and Acrylonitrile Butadiene Styrene (ABS) plastic, but are not so limited. The energy director guides are manufactured using any of a number of techniques and materials known in the art. For example, the energy director guide of an embodiment can be formed using a single-piece molded design. Further, the energy director guide of alternative embodiments can be formed using two or more separate pieces assembled to form the guide using techniques known in the art.

While six (6) channels are shown for illustrative purposes, alternative embodiments can include differing numbers of channels. One alternative embodiment includes four (4) channels, while another alternative embodiment includes eight (8) channels. The spacing among the channels 202-212 varies according to the total number of energy directors received in the energy director guide 102, as described further below. Generally, to account for electromagnetic coupling among the energy directors when the energy directors are coupled to the generator, the relative spacing among the center-most channels (206 and 208 in this embodiment) is largest while relative spacing among the end-most channels (202/204 and 210/212 in this embodiment) is smallest.

As described above, uniform energy distribution is important when generating an avascular volume of tissue suitable for bloodless or near-bloodless resection. The energy director guide 102 described herein provides uniform energy distribution via the energy directors using a channel spacing, and consequently an energy director configuration, that accounts for electromagnetic coupling effects among neighboring energy directors. The energy director guide 102 of an embodiment includes six (6) channels 202-212 that, in operation, receive three (3) pairs of bipolar energy directors. The spacing between channels 202 and 204 is approximately 0.2995 inches. The spacing between channels 204 and 206 is approximately 0.3285 inches. The spacing between channels 206 and 208 is approximately 0.3937 inches. The spacing between channels 208 and 210 is approximately 0.3285 inches. The spacing between channels 210 and 212 is approximately 0.2995 inches.

Figure 4A:
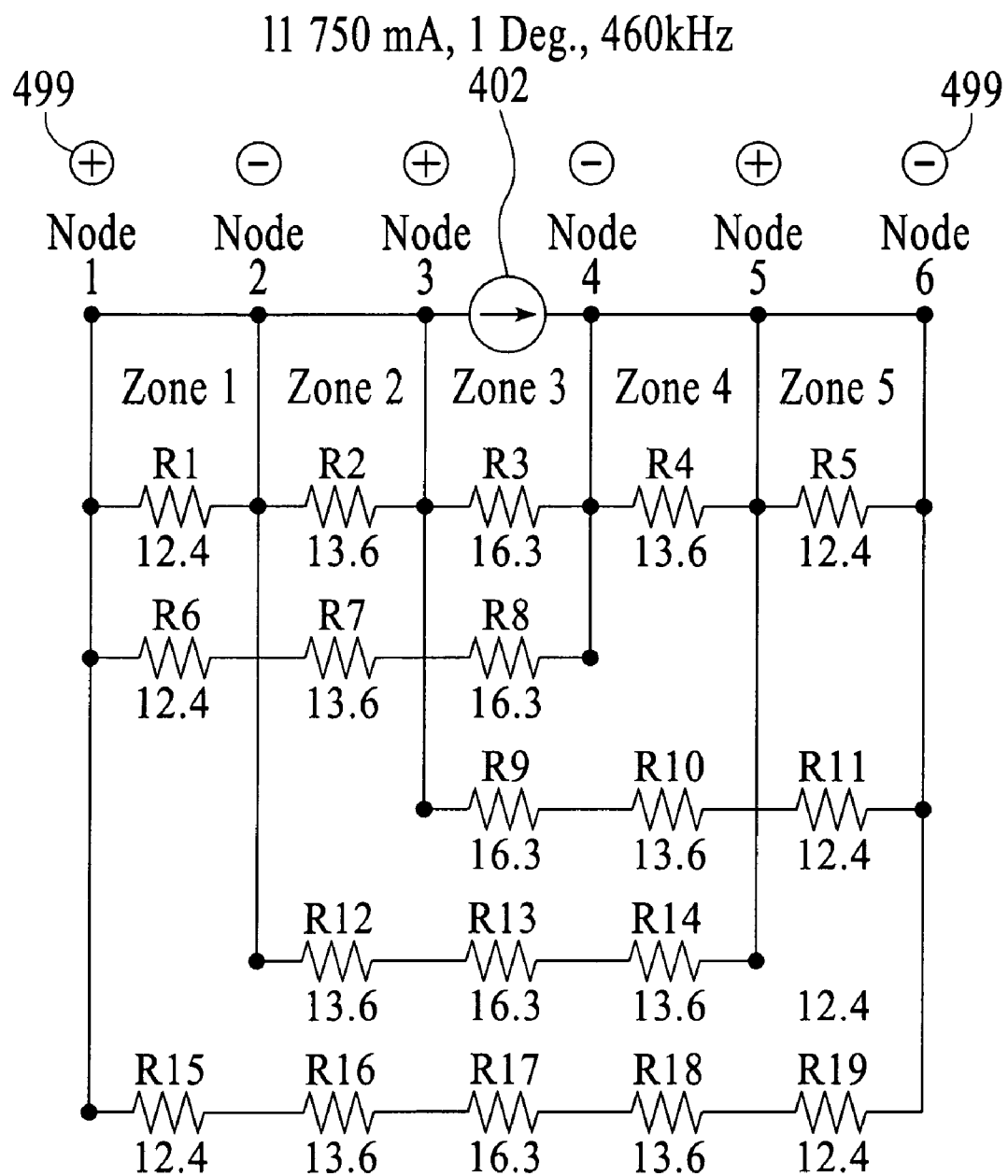
FIG. 4A shows a resistive network model for an energy director configuration including six (6) energy directors, under the embodiment of FIGS. 2 and 3.

The guide channel spacing that provides relatively uniform energy distribution is generated using resistive network models, but is not so limited. FIG. 4A shows a resistive network model 400 for an energy director configuration including six (6) bipolar energy directors, under the embodiment of FIGS. 2 and 3. Each of the six bipolar energy directors is represented by one of nodes 1-6, wherein each node is assigned an alternating polarity 499, but the polarity assigned in this example is not limiting. The model 400 includes a number of resistors R1-R19 coupled in various configurations among nodes 1-6 and current source 402, as described further below. The current source 402 is arbitrarily selected to produce 750 milliamps (mA) of current, but the model is not so limited.

Generally, the resistor configurations of the model 400 simulate the relative power dissipation, including the coupling effects among the various combinations of alternating polarity nodes, in the tissue volumes ("zones") between the energy directors (nodes), as further described below. Given that biological tissue has a resistivity (resistance per unit volume) that is proportional to the spacing between energy directors, the resistor values of the model are iteratively varied to represent different channel spacing.

Figure 4B:
FIG. 4B shows a table including power dissipation values corresponding to an energy director configuration providing balanced energy, under the embodiment of FIG. 4A.

With reference to FIG. 4A, resistor R1 models the power dissipation in zone 1 as a result of current flowing between nodes 1 and 2. Likewise, resistors R2, R3, R4, and R5 each model the power dissipation as a result of current flowing between the nodes that define each of zones 2-5, respectively. The series combination of resistors R6, R7, and R8 couple between nodes 1 and 4 and model the power dissipation across zones 1, 2, and 3 as a result of the current flowing between nodes 1 and 4. The series combination of resistors R9, R10, and R11 couple between nodes 3 and 6 and model the power dissipation across zones 3, 4, and 5 as a result of the current flowing between these nodes. The series combination of resistors R12, R13, and R14 couple between nodes 2 and 5 and model the power dissipation across zones 2, 3, and 4 as a result of the current flowing between nodes 2 and 5. Finally, the series combination of resistors R15, R16, R17, R18, and R19 couple between nodes 1 and 6 and model the power dissipation across zones 1, 2, 3, 4, and 5 as a result of the current flowing between nodes 1 and 6. FIG. 4B shows a table 450 including power dissipation values corresponding to an energy director configuration providing balanced energy, under the embodiment of FIG. 4A.

FIG. 4C is a table 480 including power dissipation and spacing information corresponding to an energy director configuration providing balanced energy, under the embodiment of FIG. 4A. This table 480 includes total power dissipation 482 for each zone of the resistive network model 400. The balanced energy director configuration uses non-uniform channel spacing in the energy director guide to account for the effects of electromagnetic coupling, as described above, under the embodiment of FIG. 2. In determining the total power dissipation per zone 482, the resistor values for the zones of an array are varied iteratively until the total power dissipation per zone 482 is approximately equal; the spacing per zone is proportional to the resistor values. The total power dissipation across zones 1-5 in a balanced energy director configuration is approximately 246 milliwatts (mW), 248 mW, 250 mW, 248 mW, and 246 mW, respectively, but is not so limited. Consequently, the power dissipation or distribution across the zones is approximately uniform.

Using the final values for the total power dissipation per zone 482, spacing ratios per zone 484 and 486 are generated. In an embodiment, two different spacing ratios per zone 484 and 486 are generated, but the embodiment is not so limited. A first spacing ratio per zone 484 references the spacing of the zones to the proximal-most/distal-most zones (zones 1 and 5) of the array, and a second spacing ratio per zone 486 references the spacing of the zones to the center zone (zone 3) of the array. Note, however, that the spacing ratios per zone can be referenced to any zone of the array in alternative embodiments.

Using either of the spacing ratios per zone 484 and 486, the relative spacing among the channels is determined by assigning a reference spacing value to the reference zone (the zone for which the spacing ration is one (1)). The spacing values for all other zones of the array are then each determined using the spacing ratio for each associated zone as a multiplier against the reference spacing value. Reference spacing values are selected using techniques known in the art, wherein the largest spacing value between the energy directors of an array is approximately in the range of 0.75 cm to 2.00 cm, but the embodiment is not so limited.

Alternative embodiments of the tissue ablation system include differing numbers of energy directors and, therefore, differing numbers of channels in the energy director guide. For example, one alternative embodiment includes an energy director guide having a series of eight (8) channels that receive energy directors of alternating polarity. As described above, the channel spacing in this alternative embodiment is also determined using a resistive network model simulation, but is not so limited.

Figure 5A:
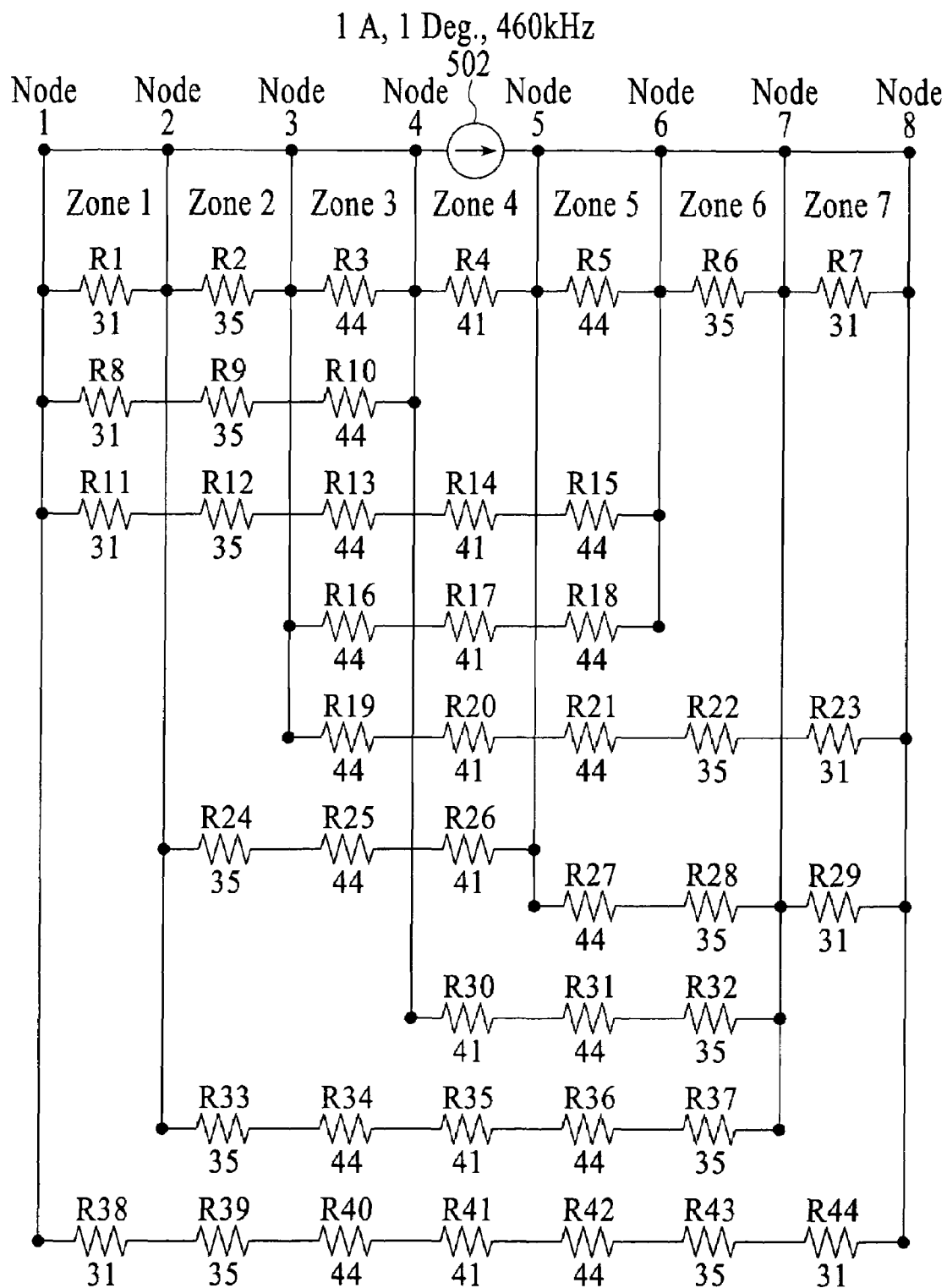
FIG. 5A shows a resistive network model for an energy director configuration including eight (8) energy directors, under an alternative embodiment.

FIG. 5A shows a resistive network model 500 for an energy director configuration including eight (8) bipolar energy directors, under an alternative embodiment. Extrapolating from the embodiment of FIG. 2, the energy director guide of this example includes eight (8) channels, each of which receive an energy director. Each of the eight bipolar energy directors is represented by one of nodes 1-8, wherein each node is assigned an alternating polarity. The model 500 includes a number of resistors R1-R44 coupled in various configurations among nodes 1-8 and current source 502, as described further below. The current source 502 is arbitrarily selected to produce one (1) amp of current, but the model is not so limited.

Referring to FIG. 5A, resistor R1 models the power dissipation as a result of current flowing between nodes 1 and 2. Likewise, resistors R2, R3, R4, R5, R6, and R7 each model the power dissipation as a result of current flowing between the nodes that define each of zones 2-7, respectively. The series combination of resistors R8, R9, and R10 couple between nodes 1 and 4 and model the power dissipation across zones 1, 2, and 3 as a result of the current flowing between nodes 1 and 4. The series combination of resistors R11, R12, R13, R14, and R15 couple between nodes 1 and 6 and model the power dissipation across zones 1, 2, 3, 4, and 5 as a result of the current flowing between nodes 1 and 6.

Continuing, the series combination of resistors R16, R17, and R18 couple between nodes 3 and 6 and model the power dissipation across zones 3, 4, and 5 as a result of the current flowing between nodes 3 and 6. The series combination of resistors R19, R20, R21, R22, and R23 couple between nodes 3 and 8 and model the power dissipation across zones 3, 4, 5, 6, and 7 as a result of the current flowing between nodes 3 and 8. The series combination of resistors R24, R25, and R26 couple between nodes 2 and 5 and model the power dissipation across zones 2, 3, and 4 as a result of the current flowing between nodes 2 and 5. The series combination of resistors R27, R28, and R29 couple between nodes 5 and 8 and model the power dissipation across zones 5, 6, and 7 as a result of the current flowing between nodes 5 and 8.

Figure 5B:
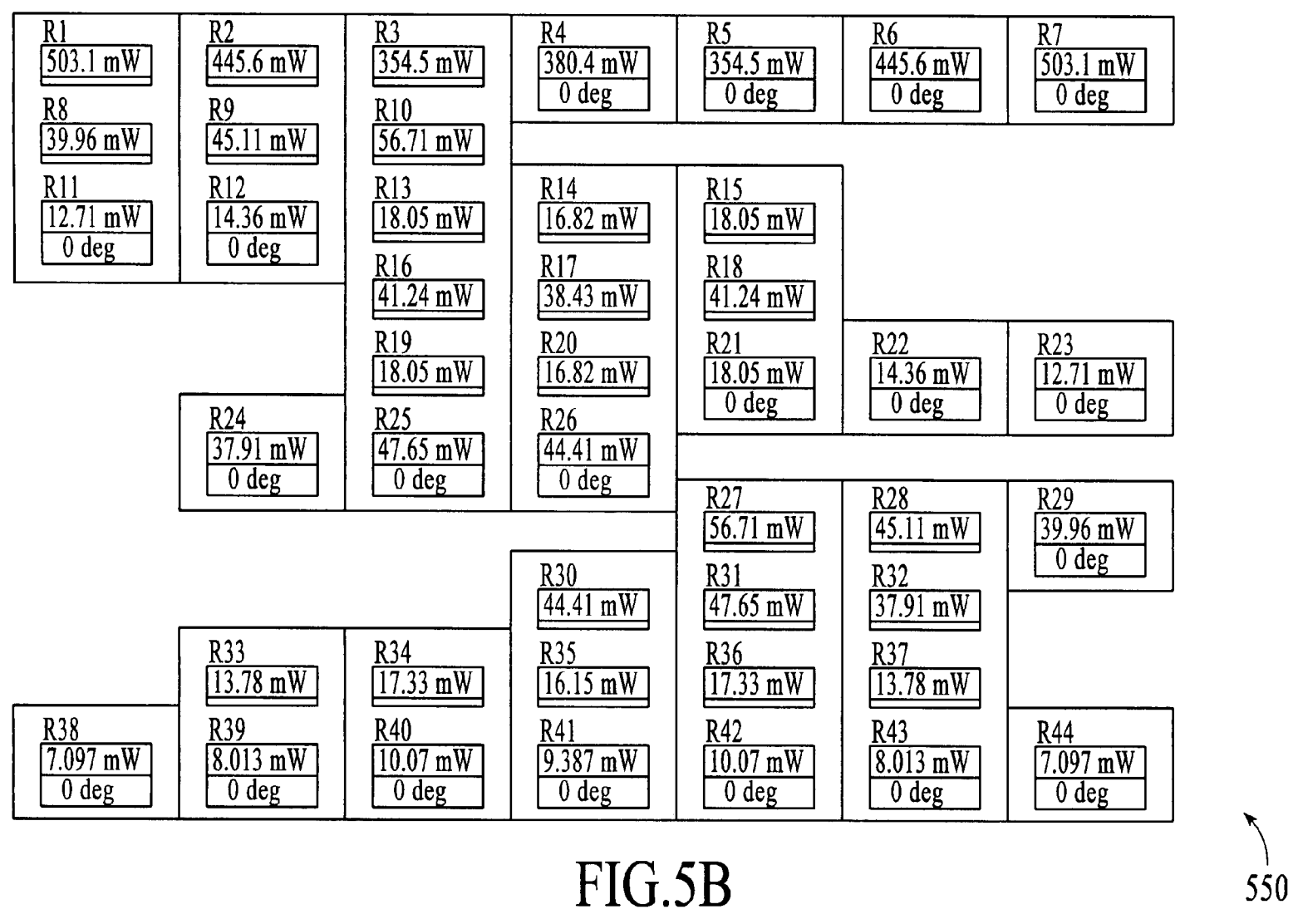

Further, the series combination of resistors R30, R31, and R32 couple between nodes 4 and 7 and model the power dissipation across zones 4, 5, and 6 as a result of the current flowing between nodes 4 and 7. The series combination of resistors R33, R34, R35, R36, and R37 couple between nodes 2 and 7 and model the power dissipation across zones 2, 3, 4, 5, and 6 as a result of the current flowing between nodes 2 and 7. Finally, the series combination of resistors R38, R39, R40, R41, R42, R43, and R44 couple between nodes 1 and 8 and model the power dissipation across zones 1, 2, 3, 4, 5, 6, and 7 as a result of the current flowing between nodes 1 and 8. FIG. 5B shows a table 550 including power dissipation values corresponding to an energy director configuration providing balanced energy, under the embodiment of FIG. 5A.

FIG. 5C is a table 580 that includes power dissipation information 582 and spacing information 584 and 586 corresponding to an energy director configuration providing balanced energy, under the embodiment of FIG. 5A. This power dissipation table 580 includes total power dissipation 582 for each zone of the resistive network model 500. The balanced energy director configuration uses non-uniform channel spacing in the energy director guide to account for the effects of electromagnetic coupling, as described above. The total power dissipation across zones 1-7 is approximately 563 mW, 565 mW, 564 mW, 567 mW, 564 mW, 565 mW, and 563 mW, respectively. Consequently, the power dissipation or distribution across the zones is approximately uniform.

The embodiments described above with reference to FIGS. 2, 3, 4, and 5 provide approximately uniform power distribution among the tissue zones of a target tissue volume. However, as power is proportional to the product of voltage and current, alternative embodiments of the energy director array are configured to provide approximately uniform current density through the target tissue volume. As such, the tissue ablation systems of various alternative embodiments generate avascular volumes of coagulated tissue using approximately uniform current density. The energy director guide channel spacing that provides uniform current density is determined using resistive network models, as above, but is not so limited.

Figure 6A:
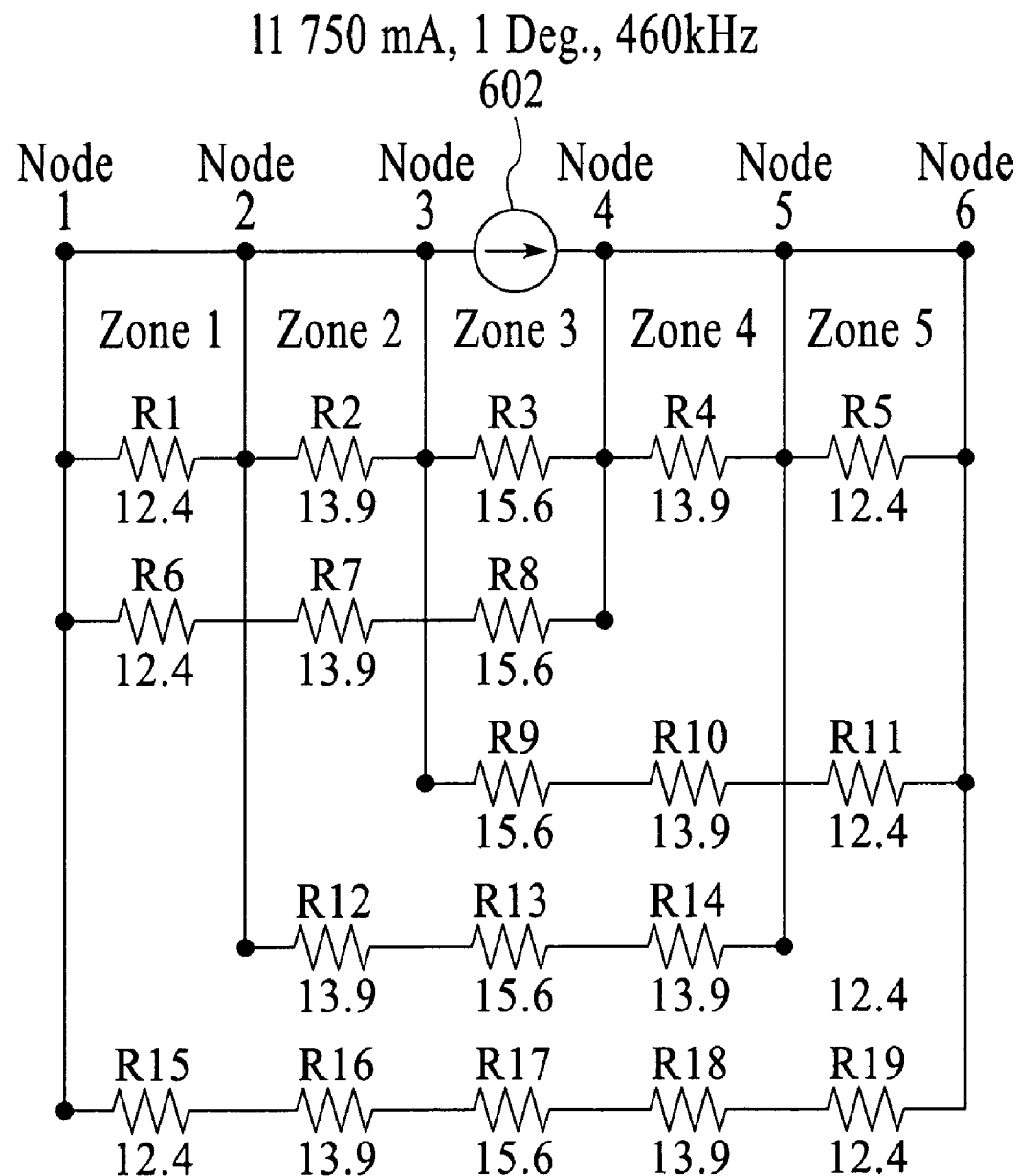
FIG. 6A shows a resistive network model for an energy director configuration including six (6) energy directors (five zones), under an alternative embodiment.

The guide channel spacing that provides relatively uniform current density is generated using resistive network models, but is not so limited. FIG. 6A shows a resistive network model 600 for an energy director configuration including six (6) bipolar energy directors, under an alternative embodiment of FIGS. 2 and 3. Each of the six bipolar energy directors is represented by one of nodes 1-6, wherein each node is assigned an alternating polarity. The model 600 includes a number of resistors R1-R19 coupled in various configurations among nodes 1-6 and current source 602, as described above with reference to FIG. 4A. The relative power dissipation among the different zones is proportional to the current density in the associated tissue zones. The current source 602 is arbitrarily selected to produce 750 milliamps (mA) of current, but the model is not so limited. FIG. 6B shows a table 650 including power dissipation information corresponding to an energy director configuration providing balanced energy, under the embodiment of FIG. 6A.

FIG. 6C is a table 680 including current density and spacing information corresponding to an energy director configuration that provides balanced energy, under the embodiment of FIG. 6A. This table 680 includes the current density per zone 682 for the zones of the resistive network model 600. The balanced energy director configuration uses non-uniform channel spacing in the energy director guide to account for the effects of electromagnetic coupling, as described above. In determining the current density per zone 682, the resistor values for the zones of an array are varied iteratively until the current density per zone 682 is approximately equal; the channel spacing information is proportional to and derived from the final resistor values that provide approximately uniform current density. The current density per zone across zones 1-5 is approximately 15.85 milliamps (mA)/spacing value, 15.8446 mA/spacing value, 15.80769 mA/spacing value, 15.8446 mA/spacing value, and 15.85 mA/spacing value, respectively, but is not so limited. Consequently, the current density across the zones is approximately uniform.

Using the current density per zone 682, spacing ratios per zone 684 and 686 are generated. In an embodiment, two different spacing ratios per zone 684 and 686 are generated, but the embodiment is not so limited. A first spacing ratio per zone 684 references the spacing of the zones to the proximal-most/distal-most zones (zones 1 and 5) of the array, and a second spacing ratio per zone 686 references the spacing of the zones to the center zone (zone 3) of the array. Note, however, that the spacing ratios per zone can be referenced to any zone of the array in alternative embodiments.

Using either of the spacing ratios per zone 684 and 686, the relative spacing among the channels is determined by assigning a reference spacing value to the reference zone (the zone for which the spacing ration is one (1)). The spacing values for all other zones of the array are then each determined using the spacing ratio for each associated zone as a multiplier against the reference spacing value. Reference spacing values are selected using techniques known in the art.

Alternative embodiments of the tissue ablation system include differing numbers of energy directors and, therefore, differing numbers of channels in the energy director guide. As described above, the channel spacing in these alternative embodiments is also determined using a resistive network model simulation, but is not so limited.

Figure 7:
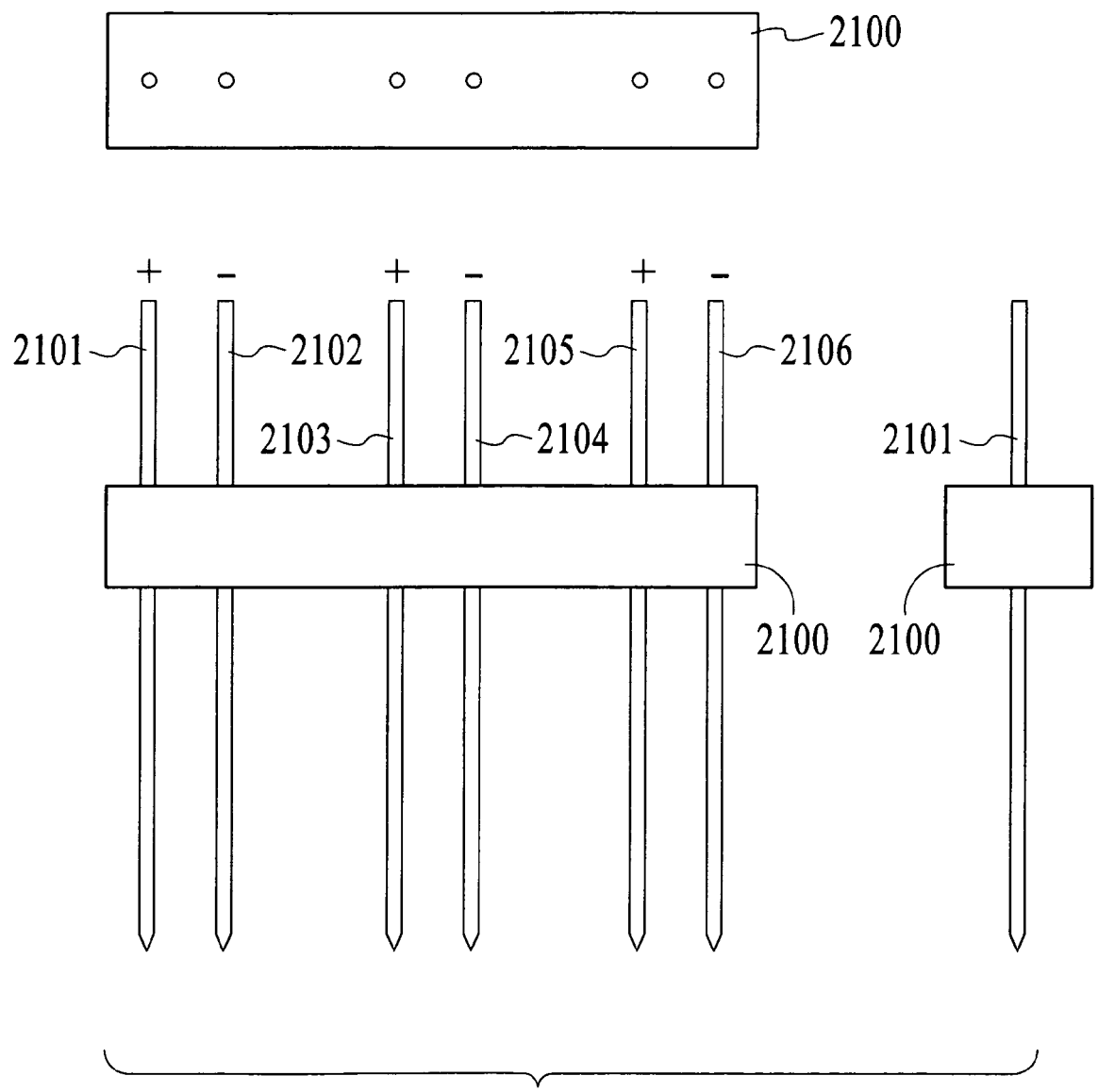
FIG. 7 is an energy director guide and energy directors, under an alternative embodiment.

FIG. 7 is a side view, end view, and top view of an energy director guide 2100 and two or more pair of bipolar energy directors 2101-2106, under an alternative embodiment. The energy director guide 2100 supports energy director configurations that provide approximately uniform energy distribution and/or current density, and thus more uniform temperatures, through the target tissue volume. The energy director guide 2100 configures the energy directors 2101-2106 in a linear row, and the energy directors 2101-2106 alternate in polarity, where example polarities are shown, but the embodiment is not so limited. While three pairs of energy directors 2101-2102, 2103-2104, 2105-2106 are shown, the embodiment is not so limited.

The energy director guide 2100 supports generally uniform energy distribution in the target tissue using relatively smaller spacing between the energy directors of a pair and relatively larger spacing between the pairs of energy directors (also referred to as distinct pairs). For example, a first spacing is used between each of energy directors 2101 and 2102, 2103 and 2104, and 2105 and 2106, while a second spacing is used between energy directors 2102 and 2103, and 2104 and 2105. In an embodiment, the spacing between the pairs of energy directors is approximately 1.5 to 2 times the spacing between the energy directors of a pair, but the embodiment is not so limited.

The configuration supported by the energy director guide 2100 results in a highly favored electrical path between the energy directors of the distinct pairs. The favored electrical path results in a large portion of the electrical energy flowing between the energy directors of the distinct pairs (between energy director pairs 2101/2102, 2103/2104, and 2105/2106 in this example), thereby producing an ablation in the tissue between the distinct pairs. Once the ablation between the pairs is formed the impedance in this tissue begins to rise. As the impedance rises, the alternate path to the opposite polarity energy director in the adjacent distinct pair becomes more and more favorable (between energy directors 2102/2103 and 2104/2105 in this example). As time progresses the impedance within the pairs (2102/2103 and 2104/2105) continues to increase resulting in the establishment of new pairs (2102/2103 and 2104/2105). This process continues until the entire ablation is complete.

The energy director guide of an alternative embodiment is reconfigurable to support a number of energy director configurations. For example, the energy director guide can include channels that are moveable between a number of pre-specified locations in the energy director guide so that placement of the channels in a first set of pre-specified locations along the guide supports the six energy guide configuration described above, and placement of the channels in a second set of pre-specified locations along the guide supports the eight energy guide configuration described above. Using this embodiment, a user can support many different energy director configurations with a single energy director guide.

Referring again to FIG. 1, the energy director guide of an embodiment independently couples each of the energy directors to the generator via the energy director guide. Further, the energy director guide independently secures a position of each of the energy directors in the target tissue.

Figure 8:
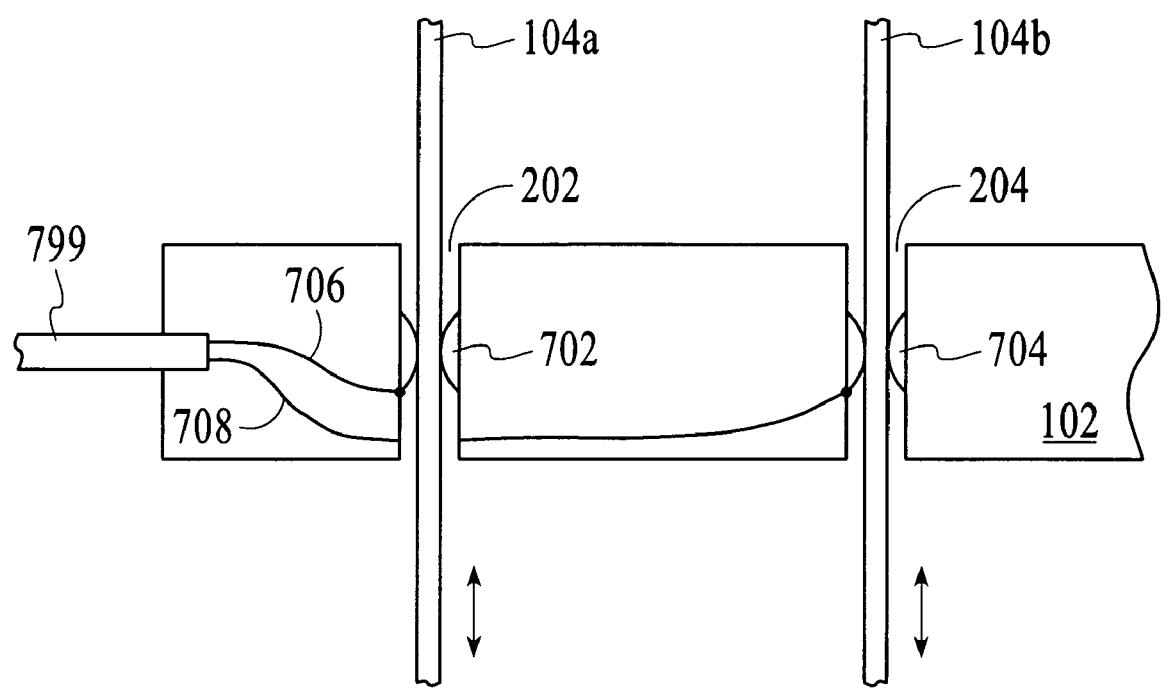
FIG. 8 is a side view of an energy director guide using direct coupling, under an embodiment.

Regarding electrical coupling of the energy directors to the generator, the energy director guide of an embodiment uses direct electrical coupling, while alternative embodiments use indirect electrical coupling. FIG. 8 is a side view of an energy director guide 102 using direct coupling, under an embodiment. Each channel 202 and 204 of the guide 102 includes one or more contacts 702 and 704 that couple conductors 706 and 708 of an energy conduit 799 from the generator (not shown) directly to the corresponding energy director 104a and 104b. When using bipolar energy directors, for example, a first conductor 706 carrying signals of a first polarity couples to a first energy director 104a via a first contact 702. Likewise, a second conductor 708 carrying signals of a second polarity couples to a second energy director 104b via a second contact 704. The contacts of an embodiment are fabricated from materials with good spring and wear properties including, for example, stainless steel and beryllium copper. Furthermore, the contacts of alternative embodiments can also secure or assist in securing a position of the energy directors, but are not so limited.

Figure 9:
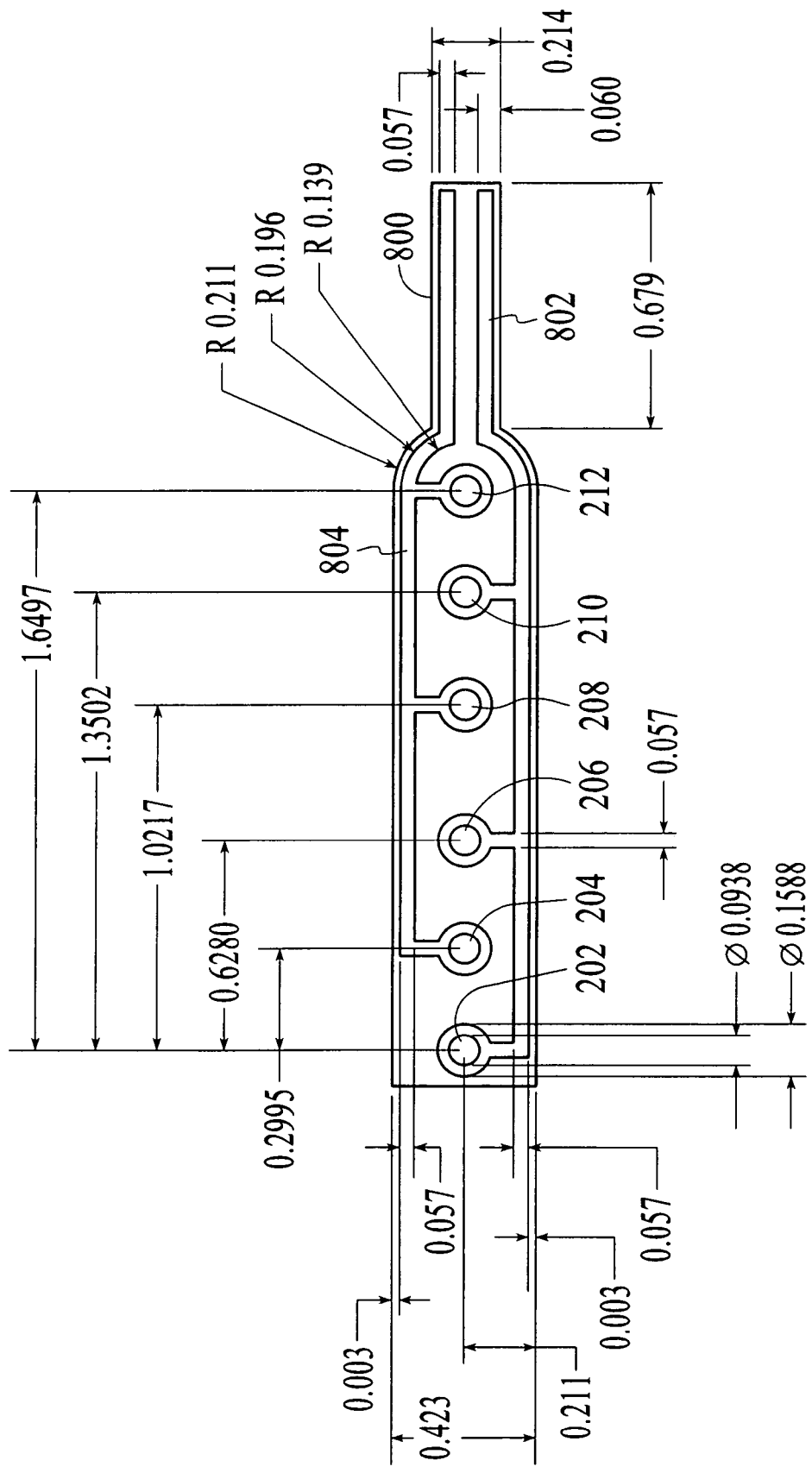
FIG. 9 is a schematic of a circuit board for use in an energy director guide, under the embodiment of FIG. 2.

FIG. 9 is a schematic of a circuit board 800 for use in an energy director guide, under the embodiment of FIG. 2. The circuit board 800 directly couples power signals having the appropriate polarity from a power source to the corresponding channels, and thus the corresponding energy directors, via conducting traces 802 and 804. In the circuit board 800 of an embodiment using alternating polarities, a first conducting trace 802 carries an electrical signal having a first polarity, for example a positive polarity, among the energy directors of channels 202, 206, and 210. A second conducting trace 804 carries an electrical signal having a second polarity, for example a negative polarity, among the energy directors of channels 204, 208, and 212, but the embodiment is not so limited.

Figure 10:
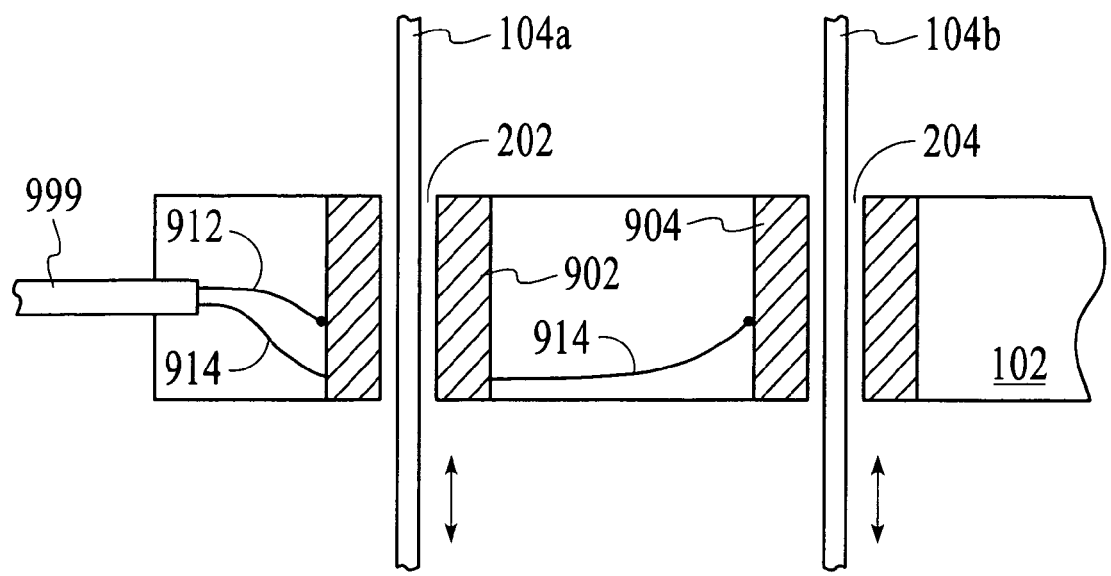
FIG. 10 is a side view of an energy director guide using indirect coupling, under an embodiment.

In an embodiment using indirect coupling, a coil of electrically conductive material that is insulated along its length is wound such that it forms a magnetic field around the electrically conductive energy director thereby inducing a current flow in the energy director. FIG. 10 is a side view of a guide 102 using indirect coupling, under an embodiment. Each channel 202 and 204 of the guide 102 includes a coil or winding of conductive material 902 and 904 that indirectly couples conductors 912 and 914 of an energy conduit 999 from the power source (not shown) to the corresponding energy director 104a-104b.

Figure 11:
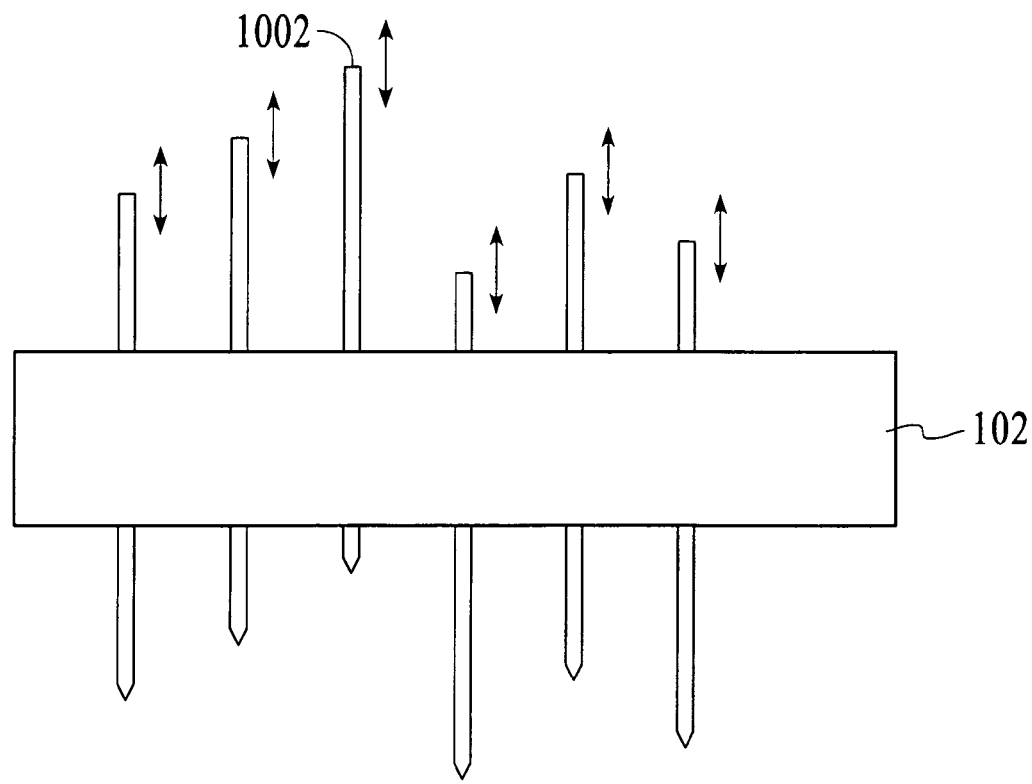
FIG. 11 shows an energy director guide that provides for independent control of the insertion depth of each energy director, under an embodiment.

As described above, the energy director guide of an embodiment supports independent control of the position of the corresponding energy directors. FIG. 11 shows a guide 102 that provides for independent control of the deployment or insertion depth of each energy director 1002, under an embodiment. The guide 102 provides independent control of the insertion of each energy director 1002 to independently variable depths within the target tissue. Energy director deployment depths are approximately in the range of one (1) centimeter to ten (10) centimeters, but are not so limited. As an example, the energy director deployment depth of one embodiment is as much as approximately four (4) centimeters, while the energy director deployment depth of an alternative embodiment is as much as approximately six (6) centimeters. Further, the energy directors of an embodiment include markings that correspond to particular deployment depths for use as an aid during insertion of the energy directors in the target tissue.

The insertion of the energy directors 1002 can be performed individually or simultaneously as appropriate to the procedure. As such, each energy director 1002 can be inserted into the target tissue to a different depth, thereby allowing the physician or clinician to avoid critical anatomical structures with the application of RF energy. This is particularly valuable since there often are present critical anatomical structures into which an energy director 1002 should not be inserted. Further, independent control of insertion depth for each energy director 1002 supports the use of various visualization methods such as ultrasound stenography, Computerized Tomography (CT), and Magnetic Resonance Imaging (MRI) in placement of the energy directors 1002 in target tissue.

The independent control of the insertion depth also supports the uniformity of heating as follows. Large amounts of localized blood flow can cause higher localized heat losses. These non-uniform heat losses can result in uneven or incomplete ablation. The tissue ablation system of an embodiment counters this effect by supporting adjustment of the amount of energy conduit engagement around that region (e.g., penetration depth). By doing this, the energy distribution can be altered to account for the additional losses.

Alteration of the energy distribution is accomplished by decreasing the penetration depth of the energy directors of the same polarity in an area of tissue adjacent to the tissue containing the large localized blood flow. This adjustment of penetration depth causes the impedance path through these adjacent energy directors to increase, thereby shifting energy to the lower impedance path which has become the area that includes the large blood flow. In the case of larger blood vessels, once they have been coagulated (as determined with the use of ultrasound Doppler and/or a Doppler flow meter, for example), the energy conduit engagement can revert to a uniform amount as described above.

Once inserted into the target tissue, components of the energy director guide exert enough force on the corresponding energy directors to secure them in the target tissue so that natural body movement will not push the energy directors out. The components of the energy director guide exert a retention force on the energy directors approximately in the range of 0.2 pound-force (lbf) to 2 lbf, but are not so limited.

Figure 12:
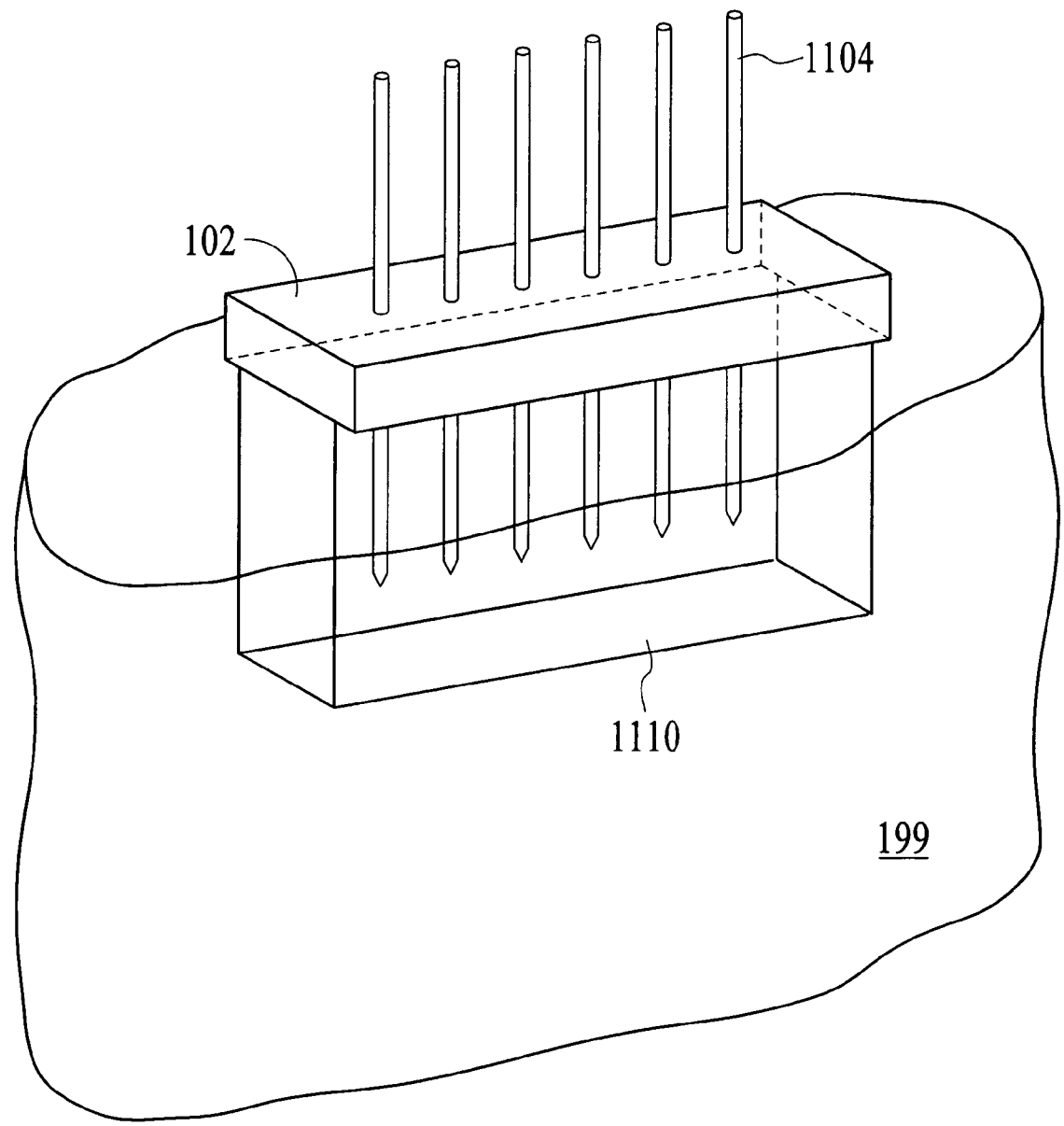
FIG. 12 and FIG. 13 show operation of the tissue ablation system to generate an avascular volume of tissue, under the embodiment of FIG. 2.

FIG. 12 shows operation of the tissue ablation system to generate an avascular volume of tissue, under the embodiment of FIG. 2. Generally, the ablation procedure begins by positioning the energy directors 1104 at a first depth in the target tissue 199. The depth shown is exemplary only, and is not a limiting depth. As such, the first depth at which the energy directors 1104 are placed is not limited to a particular depth except by the length of the energy directors 1104 used in a particular procedure or the anatomical structures present in the target tissue. Following placement of the energy directors, the user applies power to the positioned energy directors 1104, thereby ablating the corresponding volume 1110 of engaged target tissue.

Figure 13:
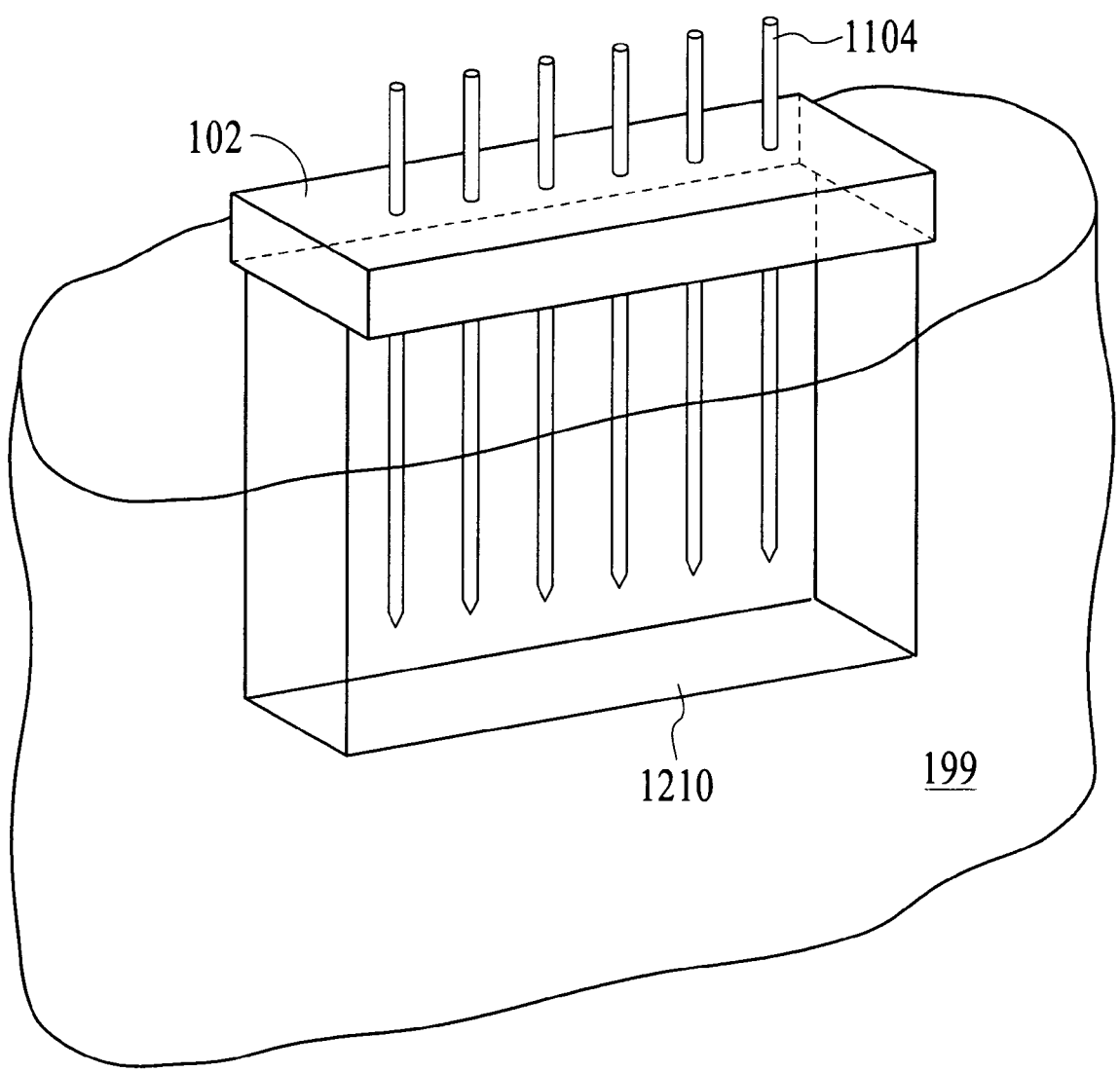

As another example in operation, the tissue ablation system can be used to incrementally ablate a volume of target tissue as the energy directors 1104 are incrementally advanced into the target tissue. FIG. 13 shows operation of the tissue ablation system to generate an avascular volume of tissue, under an alternative embodiment of FIG. 12. Referring to FIG. 13, and following ablation of the tissue volume 1110 associated with the first depth of the energy directors 1104 (FIG. 12), the energy directors 1104 are further advanced to a second depth in the target tissue 199. Following this advancement, the user couples the power to the energy directors 1104, thereby ablating the corresponding increased volume 1210 of engaged target tissue. Advancement of the energy directors 1104 continues until the entire desired volume of tissue is rendered avascular or near-avascular. The shape and size of the ablation volume 1110 and 1210 is controlled by the configuration of the electrode cluster, the geometry of the exposed energy director tips, the amount of power applied, the time duration that the power is applied, and cooling of the electrodes, to name a few.

The tissue ablation system provided herein along with the associated methods and procedures is particularly useful in controlling and optimizing several critical parameters of a tissue ablation procedure including energy density, thermal load from the surrounding tissue, and the electrical impedance of the tissue. The tissue ablation procedure includes the thermal coagulation necrosis of soft tissues as an aid during tissue resection. Methods of applying an amount of power or energy in a balanced fashion using the tissue ablation system to create a uniform section of coagulated tissue are provided below, where the power can be in any form that causes tissue to heat. The balanced fashion of power application is the delivery of power in such a way as to generate a reasonably uniform volume of coagulated tissue resulting in hemostasis. This is accomplished by generating a reasonably uniform temperature increase in the target tissue.

The tissue ablation system of an embodiment generates a uniform volume of coagulated tissue that is a generally rectangular volume, but the embodiment is not so limited. The rectangular volume can, for example, have a width approximately in the range of 0.5 cm to 1 cm but is not so limited. The rectangular volume overcomes the problems in prior art tissue ablation systems that might attempt to generate shaped ablation planes/volumes using a series of spherical ablation volumes.

As a result of their geometry, attempts to form a rectangular ablation plane using a series of overlapping spheres will result in a very irregular surface in the target tissue. This irregular surface causes problems when attempting to resect within such an irregular plane or surface of ablated tissue that was generated from a series of spheres. If the spheres of ablated tissue are large enough to fully include the desirable rectangular plane of ablated tissue, then too much tissue will have been ablated. This excessive amount of dead tissue can subsequently lead to significant and possibly life-threatening problems for the patient. If on the other hand, the ablation spheres are sized so that their maximum diameter is within the desirable rectangular plane, then a significant portion of the hemostasis is lost due to the large amount of unablated tissue that remains along the uneven edges of the overlapping spheres. In this case the reason for creating the ablation is largely reduced or eliminated. In addition, the use of monopolar energy to create the ablation spheres, by the very nature of monopolar energy, results in a less defined and confined ablation plane.

The typical approach of coagulating tissue by applying a uniform amount of power to a uniform volume of tissue is not the best solution because it does not result in a uniform increase in tissue temperature. The problems inherent in the typical systems and methods relate to several issues. First, when the energy density is too low the thermal effect cannot be achieved. Likewise, when the thermal load from the surrounding tissue is too large the thermal effect will also not be achieved. Also, low electrical tissue impedance makes it difficult to heat since the dissipated power is proportional to the tissue impedance. Very low or high impedance will also be difficult for some power supplies to deliver the required energy.

In one typical configuration known in the art, for example, several energy conduits can be placed within a target tissue at a uniform separation. When an energy source such as radio frequency (RF) current is uniformly applied in a bi-polar fashion to this arrangement of energy conduits, current flowing from the outer energy conduits distributes inward to the opposite polarity energy conduit. Similarly, current flowing from the other energy conduits also flows to the opposite polarity energy conduit. As can be shown and demonstrated, this configuration results in a non-uniform overlapping of current flow. This uniform placement of energy conduits with a uniform amount of energy delivery does not therefore result in a uniform current distribution (or current density), a uniform energy dissipation, or a uniform increase in temperature within the tissue.

Figure 14:
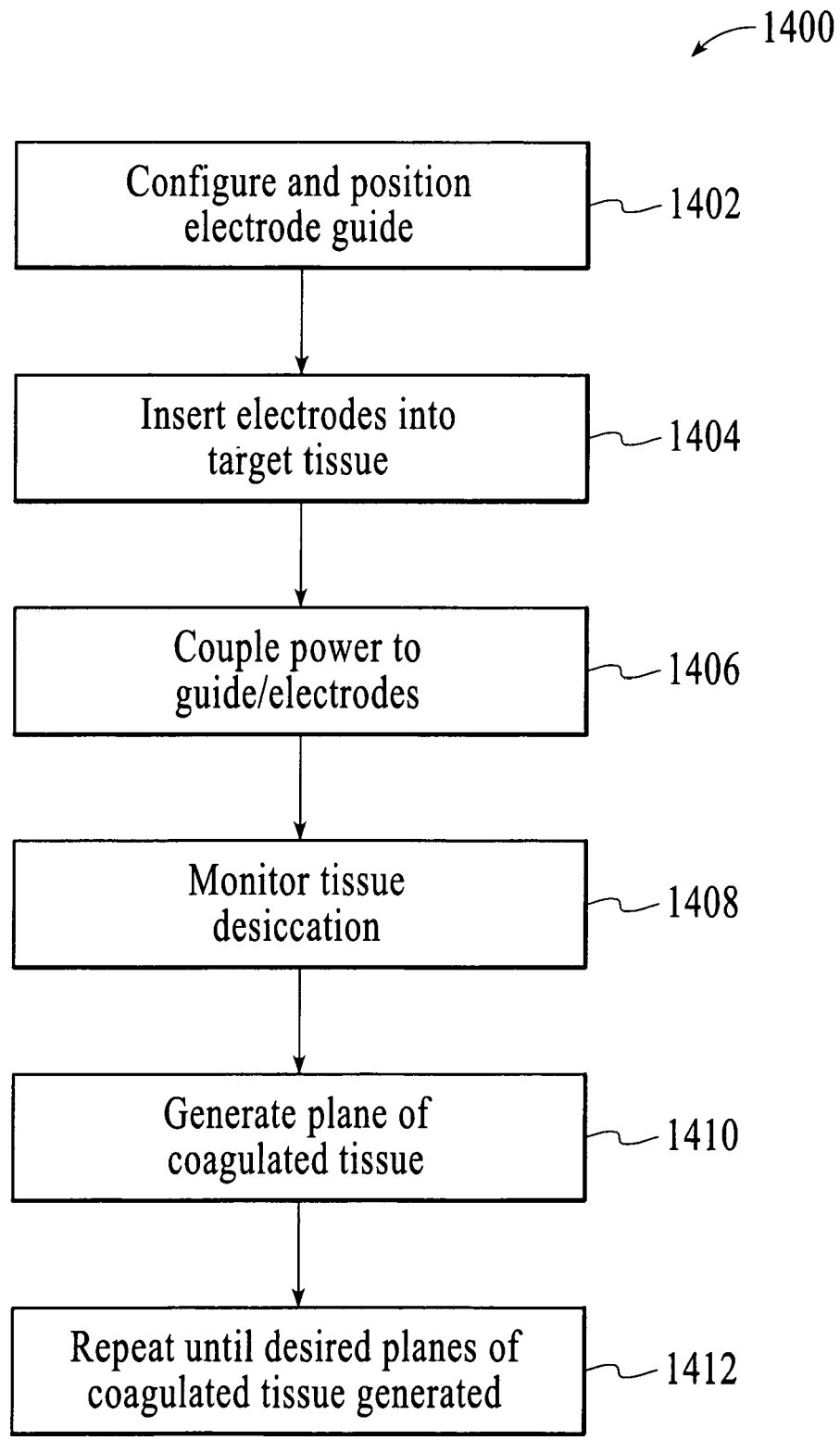
FIG. 14 is a flow diagram for the operation of the tissue ablation system, under an embodiment.

The energy conduit configurations and methods provided by the tissue ablation system of an embodiment, however, provide more uniform tissue temperature in the target tissue, thereby reducing and/or eliminating many of these problems. FIG. 14 is a flow diagram 1400 for operation of the tissue ablation system, under an embodiment. In operation, and depending on the clinical conditions or requirements, a user selects an appropriate configuration of the electrodes, at block 1402. This selection includes, for example, determinations as to the following factors: (i) the number of electrodes in the cluster; (ii) the relative geometry, individual size, and tip exposure of the electrodes; (iii) the geometry of the target tissue region and identification of any tissue regions to be avoided; and (iv) selecting cooled or non-cooled electrodes. Further, the selection can include processing image scan data from a CT scan, MRI, ultrasound, and/or other type of scanning device to determine the position of a targeted volume such as a tumor within the patient's body and the desired approach, placement, size, and number of electrodes.

The positioning of the electrodes in an embodiment is preplanned, for example using a workstation, and the heat isotherms and ablation volume and time-course of the ablation are determined. Based on historical or empirical information, the user may determine the desired power to be delivered to the tissue, the temperature as measured by the electrode or measured elsewhere in the tissue by either integrated temperature sensors in the energy directors or satellite temperature-sensing electrodes, the desired time duration of heating, and the characteristics of impedance, to determine energy application timing parameters and control against charring and other undesired effects.

Further, the selection of an electrode configuration under an embodiment includes sizing of the electrodes based on the target organ. For example, the user can estimate a transverse dimension of the target organ. Using the estimated dimension, the user sizes the electrodes individually or as a group so that the electrodes do not extend beyond the target organ when fully inserted in the target organ.

Following the configuration and planning, the user positions the energy director guide, and inserts the electrodes into the target tissue, at block 1404. The electrodes can be placed individually or in unison within the body tissue, as described herein. Real-time imaging can be used, for example CT, MRI, and/or ultrasound, during placement of the electrodes to determine their proper position within a targeted volume of tissue. The user inserts the electrodes to a desired depth. Additionally, if the electrodes are used with coolant, the user applies the coolant as appropriate.

During some procedures involving the tissue ablation system the user separates the target organ from one or more adjacent organs, but the embodiment is not so limited. This is done to prevent the electrodes from piercing the adjacent organs upon or during insertion into the target organ. Alternatively, the user can place a shield between the target organ and any adjacent organs to protect the adjacent organs from penetration by the electrodes.

The user couples or applies power from the generator to the energy director guide and the electrodes, at block 1406. Alternatively, the power is coupled directly to the electrodes. While power is described in this example, various alternative embodiments can, instead of using power as the controlling parameter, use current, voltage, impedance, temperature, time, and/or any combination of these, to control the tissue ablation process. The power can be coupled to all of the electrodes in unison, or sequentially in a predetermined sequence, as appropriate to the treatment procedure and/or the target tissue type. Likewise, the insertion depth of the electrodes and the amount of power coupled to the electrodes is varied according to the treatment procedure and/or the target tissue type.

The application of power can be controlled automatically and/or manually under any of a number of procedures, as described in detail below. When using automatic control, the process is controlled according to one or more algorithms or controllers integral to the generator system itself or by one or more distributed algorithms and/or controllers coupled among the components of the tissue ablation system. Further, the application of power to the electrodes can be controlled in response to at least one parameter that includes time, temperature, impedance, and/or other known feedback parameters associated with the ablation process.

The thermal coagulation of tissue is monitored, at block 1408, using the feedback parameters appropriate to the equipment and procedure being used. Coupling power to the energy director guide/electrodes, at block 1406, results in generation of a plane of coagulated tissue in the target tissue, at block 1410. In an embodiment, pre-specified parameters and thresholds appropriate to the equipment and procedure are used to determine when the plane of coagulated tissue has been generated. The user repeats various portions of the procedure, as appropriate to the target tissue, until a plane of coagulated tissue having the appropriate size and shape is generated, at block 1412.

Operation of the tissue ablation system of an embodiment includes the use of a temperature feedback system in which temperature is measured at one or more locations within the tissue and the delivered power is varied or altered (i.e., increased, decreased, or maintained) to maintain the correct level of power delivery. Using this method, the target tissue is divided into quadrants or sections and the power delivery is individually varied on a section-by-section basis using the temperature feedback information. When temperature within a given section is increasing significantly beyond the other sections, the power delivery to that section is reduced sufficiently to maintain parity with the other sections or to a pre-specified target temperature. Conversely if, based on the temperature feedback information, the temperature of a section is below that of other sections of the target tissue, the power delivered to that section is increased to achieve parity with the other sections or a pre-specified target temperature.

A predetermined rate of temperature increase can also be used to make the temperature in the individual sections of the target tissue comparable to resulting temperatures in other sections of the target tissue. For example, if the predetermined rate of temperature increase is approximately in the range of 35 to 40 degrees Celsius per minute, then power would be applied at an initial rate and the increase in temperature would be evaluated. If as time progresses the temperature in this individual section of target tissue is low, power to that section is increased. If the tissue temperature of a section of target tissue is increasing beyond the predetermined rate, resulting in a high temperature, the power delivery to that section is reduced. This method has the benefit of allowing a predetermined rate to be selected for a specific tissue type and condition. Also, local variations in heat loss due to the various factors such as blood flow are more readily accounted for. In order to achieve a more uniform distribution, the number of sections per unit of target tissue can be increased. Further, a more uniform distribution can be achieved through the use of smaller predetermined temperature ranges.

Operation of the tissue ablation system of an embodiment also includes the use of variations in an amount of tissue to which a quantity of power is applied. In this method the natural flow and overlap of the delivered power is accounted for by increasing or decreasing the spacing between the energy conduits. This effectively alters the energy path, thereby increasing or decreasing the relative resistance and energy flow. This results in balanced power dissipation within the target tissue and, therefore, a uniform temperature rise. As described above, the spacing of the energy conduits in the tissue can be modeled as an electrical circuit. This model assigns a resistance value to the tissue between the energy conduits, which is proportional to the distance between the energy conduits. Analyzing this circuit allows the resistance or distance between the energy conduits to be adjusted so that a uniform amount of energy dissipation results within the tissue providing a reasonably uniform increase in temperature, as described above with reference to FIGS. 4, 5, and 6.

Generally, procedures that use the tissue ablation system of an embodiment begin with the selection of an energy conduit of a sufficiently conductive material as appropriate to the power source. The energy conduit configuration should have a sufficient interface between the energy conduits and the target tissue as appropriate for the desired rate of power delivery and the resulting temperature rise since typically the point of highest energy density exists around the energy conduit.

An inadequate interface area between the energy conduit and the target tissue for the amount of delivered power can cause a rapid increase in the desiccation and carbonization or char of the tissue around the energy conduit, the result of which tends to inhibit or stop the transfer of energy between the tissue and the energy conduit. Various additional methods can be used to help mitigate this limitation by lowering the temperature or temperature rise around the energy conduit. These mitigation methods include chilling the energy conduit or tissue around the energy conduit, and/or adding an agent around the energy conduit to reduce the energy resistance between the energy conduit and the target tissue resulting in a decrease in the power dissipation around the energy conduit.

Following selection of the energy conduits, the energy conduits are placed in a configuration that results in an approximately uniform temperature increase sufficient to cause the targeted tissue to coagulate. The number and size of energy conduits used is a function of several factors including the available energy to be delivered from the power source, the length of time for energy delivery, the desired shape of the resulting coagulated tissue, the amount of heat loss within the tissue, and the susceptibility of the tissue to charring, to name a few. Once the electrodes are placed, the operator initiates power delivery to the target tissue.

When using an power source that heats based on the electrical resistance of the tissue, for example when using RF current, a lower amount of power is delivered in the initial stages of heating, but the embodiment is not so limited. The power initially delivered is approximately in the range of 10 to 100 Watts, depending on electrode deployment depth, but is not so limited because power values depend on the amount of interface surface area between the energy conduit and the tissue (for a relatively small interface surface area the amount of power can be significantly reduced; likewise, the amount of power is increased for a relatively large interface surface area). This permits the cell membranes within the tissues and around the energy conduits to rupture and release their electrically conductive interstitial fluid. The release of the electrically conductive interstitial fluids results in lower impedance around the energy conduit and support subsequent delivery of larger amounts of power. This increase in power allows more power to be delivered and shortens the process time. In addition, this larger amount of power permits larger blood vessels to be coagulated.

Upon initiating power delivery, the temperature of the target tissue begins to rise. Factors such as local blood flow and dilatory effects in an area of the target tissue can result in an increased heat loss in the target tissue, thereby reducing the temperature rise within the tissue immediately adjacent to that area. This condition is counteracted in operation by increasing the amount of power delivered to the region containing higher local blood flow by increasing the amount of energy passing through the target tissue of that effected region.

As energy within a particular region can be increased by reducing the amount of available energy conduits of like polarity in neighboring regions, partial retraction of the neighboring energy conduits of like polarity, for example, decreases the tissue engagement surface area of those energy conduits, thereby redirecting a larger amount of energy into the region of the higher local blood flow. The delivery of more energy into the region containing the higher local blood flow subsequently offsets the additional heat loss. Once the unbalanced blood flow has been removed, by coagulation of a single large blood vessel for example, the energy conduits of the array are again placed with approximately uniform exposure.

Completion of the coagulation process in target tissue is detected in a number of ways, including the use of tissue temperature and/or tissue impedance. When using tissue temperature, the tissue temperature can be measured in a number of ways. One way to measure tissue temperature includes measuring the temperature within or around the energy conduits. This measurement technique has the value of being easy to implement because it uses the energy conduit to house and deliver at least one temperature sensor, without the need for additional materials.

The measurement of temperature via a sensor in the energy conduits, however, measures temperature in a location that is typically at or near the highest energy density; this tends to provide temperatures that are higher than those measured within target tissue removed from the immediate vicinity of the energy conduit. This issue is mitigated somewhat by using larger interfaces between energy conduits and target tissue, thereby reducing the high energy density around the energy conduit. This issue is also mitigated by, in the case of RF energy, using a bipolar energy conduit configuration. The bipolar configuration, because the energy conduits are local to the target tissue, maintains more of a "line of sight" energy dispersion resulting in a higher energy density throughout the target tissue. This is in contrast to a mono-polar arrangement in which a first polarity is used for the energy conduits local to the target tissue and a second (opposite) polarity is remotely located away from the target tissue; in this mono-polar configuration energy tends to dissipate outwardly from the energy conduits in all directions ultimately seeking the path of lowest resistance to the remote opposite polarity.

Another method for measuring tissue temperatures includes locating a temperature sensor within the target tissue, but remote to the energy conduits. This supports evaluation of temperatures in regions of relatively low energy density producing a lower or "worse case" temperature indication. Any effect of unusual heat loss such as from large blood vessels can also be noted. The measurement of tissue temperatures remote to the energy conduits includes using a fixed position for temperature measurements away from the energy conduits, or moving a temperature probe to various locations remote to the energy conduits during the procedure. Once temperatures within the target tissue reach a temperature above the tissue coagulation temperature (often at or above approximately 70 degrees Celsius) energy delivery is stopped.

Another method for determining the completion of the coagulation process includes measuring the electrical impedance within the target tissue. With the application of coagulative energy to tissue, the electrical impedance between the energy conduits and the tissue typically decreases due to release of the conductive interstitial fluid from the tissue. After this decrease in impedance, the impedance stabilizes and remains so as the tissue increases in temperature. As energy delivery to the tissue is continued after coagulation has occurred, a higher degree of tissue desiccation occurs. This desiccation is indicated by a slow increase in the impedance between the energy conduits. Therefore, the small continual increase in the tissue impedance denotes completion of tissue coagulation and the process of higher desiccation in the target tissue. Further application of energy results in a large and rapid rise of impedance denoting an unwanted transition from desiccation to carbonization or char. Thus, once the steady increase in impedance is noted energy delivery is stopped. It is assumed that the initial delivery of energy to the target tissue was low enough to prevent premature tissue charring around the energy conduits only.

Another alternative method for determining the completion of the coagulation process includes the use of temperature and tissue impedance measurements/measuring components. The temperature and tissue impedance measuring components are in a single feedback system, but the embodiment is not so limited.

Once coagulation is complete in the target tissue, the energy conduits are removed. The energy conduits are relocated to another area of target tissue and the above methods are repeated as necessary to form larger planes of coagulated tissue, as described herein. If the coagulation method uses bipolar RF energy, then one of the outer most energy conduits should be located directly adjacent to the ablation created by the previous ablation plane, but the embodiment is not so limited. Once the full length of the coagulated ablation plane is completed, tissue resection through the coagulated plane is performed.

Various alternative embodiments can simultaneously use any number of energy director guides/electrodes in a procedure in order to form volumes of coagulated tissue having shapes and sizes appropriate to the treatment procedure. Numerous alternatives would be recognized by those skilled in the art in view of the tissue ablation system described herein.

As described above, the application of power under an embodiment is controlled automatically and/or manually under a number of procedures. A first type of procedure uses a predetermined pattern of energy delivery according to a time schedule. A second type of procedure varies the application of energy to the target tissue volume in accordance with temperature information or feedback parameters of the tissue. A third type of procedure varies the application of energy to the target tissue volume in accordance with impedance information or feedback parameters of the tissue in combination with elapsed time. A fourth type of procedure varies the application of energy to the target tissue volume in accordance with impedance information or feedback parameters of the tissue. A fifth type of procedure varies the application of energy to the target tissue volume in accordance with temperature and impedance information or feedback parameters of the tissue. Each of these procedure types is described in detail below.

The first type of procedure uses a predetermined pattern of energy delivery according to a time schedule. One procedure under this first procedure type directs the user to select a predetermined power setting in accordance with a deployment depth of one or more of the electrodes in the target tissue, and then directs application of the power for a predetermined period of time. As an example, the procedure directs selection of a 15 Watt (W) power setting for a 1 centimeter (cm) electrode deployment depth, a 30 W power setting for a 2 cm electrode deployment depth, a 45 W power setting for a 3 cm electrode deployment depth, a 60 W power setting for a 4 cm electrode deployment depth, a 75 W power setting for a 5 cm electrode deployment depth, and an 85 W power setting for a 6 cm electrode deployment depth. Following selection of a power setting appropriate to the electrode deployment depth, the procedure directs application of power for a period not to exceed approximately three minutes. Upon the expiration of the three minute period, the user fully retracts the electrodes and removes the tissue ablation device. The process is repeated as appropriate to generate the desired volume of ablated tissue.

Another procedure under this first procedure type directs the user to apply predetermined amounts of power according to a time schedule and a deployment depth of one or more of the electrodes in the target tissue. As an example, for a 1 cm electrode deployment depth, the procedure directs application of 10 Watts of power for 90 seconds (secs), followed immediately by application of 15 Watts of power for 60 seconds, followed immediately by application of 20 Watts of power for 30 seconds. When using a 2 cm electrode deployment depth, the procedure directs application of 25 Watts of power for 90 seconds, followed immediately by application of 30 Watts of power for 60 seconds, followed immediately by application of 35 Watts of power for 30 seconds. When using a 3 cm electrode deployment depth, the procedure directs application of 40 Watts of power for 90 seconds, followed immediately by application of 45 Watts of power for 60 seconds, followed immediately by application of 50 Watts of power for 30 seconds. When using a 4 cm electrode deployment depth, the procedure directs application of 55 Watts of power for 90 seconds, followed immediately by application of 60 Watts of power for 60 seconds, followed immediately by application of 65 Watts of power for 30 seconds. When using a 5 cm electrode deployment depth, the procedure directs application of 70 Watts of power for 90 seconds, followed immediately by application of 75 Watts of power for 60 seconds, followed immediately by application of 80 Watts of power for 30 seconds. When using a 6 cm electrode deployment depth, the procedure directs application of 80 Watts of power for 90 seconds, followed immediately by application of 85 Watts of power for 60 seconds, followed immediately by application of 90 Watts of power for 30 seconds. Upon completion of the three power cycles appropriate to the deployment depth, the user fully retracts the electrodes and removes the tissue ablation device. The process is repeated as appropriate to generate the desired volume of ablated tissue.

This procedure under which the user applies predetermined amounts of power according to a time schedule and an electrode deployment depth is effective in coagulating many types of tissue. The staged power delivery results in delivery of smaller amounts of power at the beginning of the procedure, where the smaller amounts of power coagulate tissue having lower blood flow, for example cirrhotic tissue and fatty tissue, earlier in the procedure without flashing effects that could stop the coagulation procedure. Furthermore, the delivery of higher amounts of power later in the procedure thoroughly coagulate tissue having higher blood flows without unduly prolonging the total time of the procedure.

The second type of procedure varies the application of energy to the target tissue volume in accordance with temperature information or feedback parameters of the tissue. This procedure includes variations in the amount of energy and/or time of energy application based on temperature information received from at least one temperature sensor in the target tissue. The amount of energy and/or time of energy application are controlled in accordance with pre-specified temperature parameters appropriate to the target tissue type/procedure to prevent the delivery of excess energy and consequently prevents overheating and charring of the target tissue.

Figure 15:
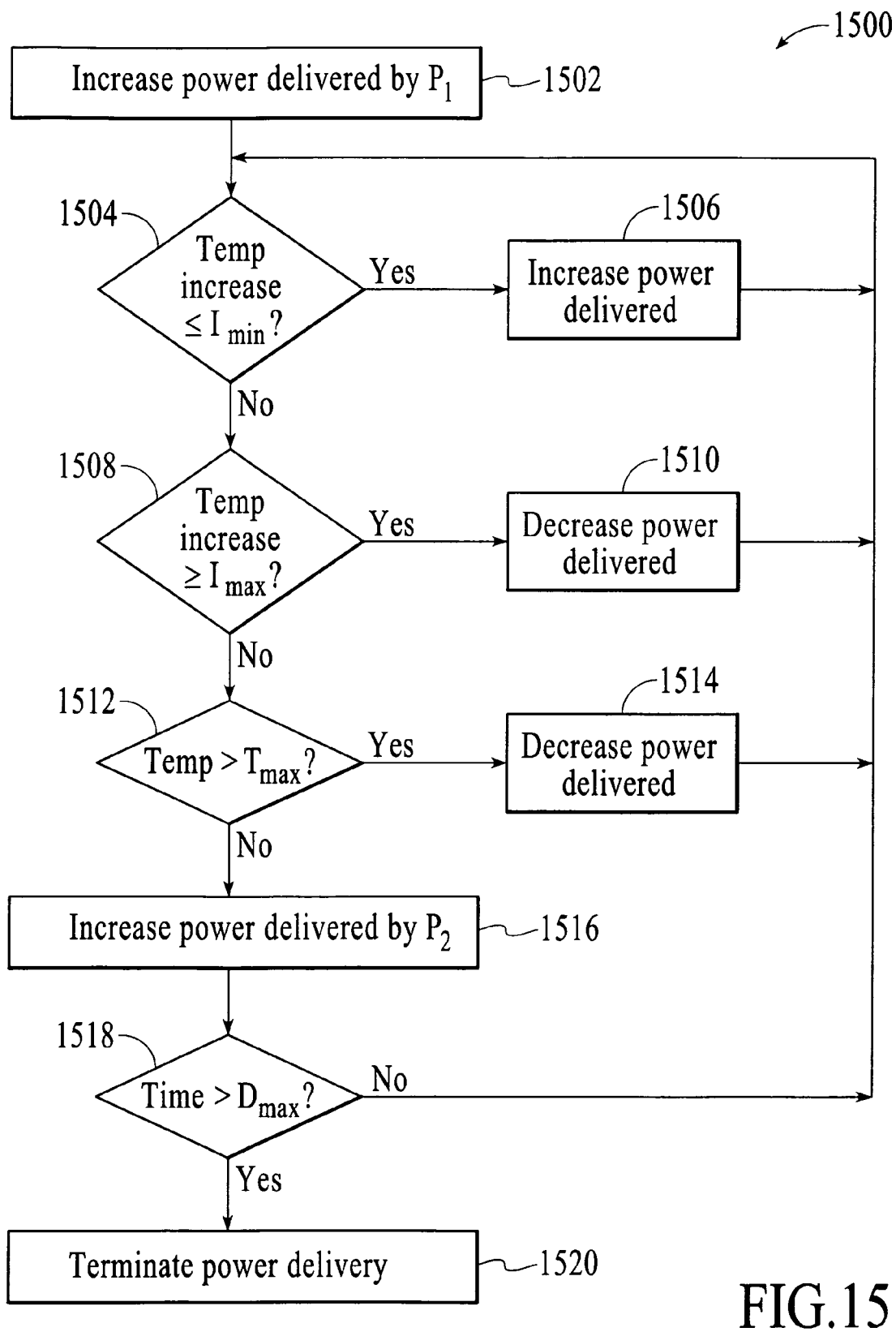
FIG. 15 is a flow diagram for controlling tissue ablation in accordance with temperature parameters, under an embodiment.

FIG. 15 is a flow diagram 1500 for controlling tissue ablation in accordance with temperature parameters, under an embodiment. Following placement of the electrodes in the target tissue, the user increases the power delivered to the target tissue by an amount $P_1$, at block 1502, where $P_1$ is approximately in the range 0.1 W/sec to 10 W/sec. A determination is made whether rates of temperature change in the target tissue are less than or equal to $I_{min}$, at block 1504, where $I_{min}$ is approximately in the range 0.1 degrees Celsius/sec to 5 degrees Celsius/sec. When rates of temperature change are less than $I_{min}$, the power delivered to the target tissue is increased, at block 1506, and operation continues at block 1504.

When rates of temperature change are greater then $I_{min}$, a determination is made whether rates of temperature change in the target tissue are greater than or equal to $I_{max}$, at block 1508, where $I_{max}$ is approximately 5 degrees Celsius/sec. When rates of temperature change are greater than $I_{max}$, the power delivered to the target tissue is decreased, at block 1510, and operation continues at block 1504.

When rates of temperature change in the target tissue are within the range bounded by $I_{min}$ and $I_{max}$, a determination is made whether a temperature of the target tissue is greater than $T_{max}$, at block 1512, where $T_{max}$ is approximately in the range 85 to 115 degrees Celsius. When a temperature of the target tissue is greater than $T_{max}$, the power delivered to the target tissue is decreased, at block 1514, and operation continues at block 1504.

When the rates of temperature change in the target tissue are within the range bounded by $I_{min}$ and $I_{max}$ and the temperature of the target tissue is less than $T_{max}$, the power delivered to the target tissue is increased by an amount $P_2$, at block 1516, where $P_2$ is approximately in the range 0.1 W/sec to 10 W/sec. Operation continues at block 1518 where a determination is made whether the elapsed time of power application to the target tissue exceeds $D_{max}$, where $D_{max}$ is a pre-specified amount of time greater than one (1) minute. When the elapsed time exceeds $D_{max}$, the application of power to the target tissue is terminated, at block 1520; otherwise, operation continues at block 1504 as described above.

An example procedure that controls tissue ablation in accordance with temperature parameters, as described above, uses the following parameter values: $P_1$ is approximately 2 W/sec; $I_{min}$ is approximately 2 degrees Celsius/sec; $I_{max}$ is approximately 5 degrees Celsius/sec; $T_{max}$ is approximately 105 degrees Celsius; $P_2$ is approximately 4 W/sec; and $D_{max}$ is approximately 3 minutes. These parameters are examples only and do not limit the embodiments described herein.

When controlling ablation using temperature information, the temperature is increased at an appropriate rate, for example a rate approximately in the range 25 degrees Celsius/minute to 100 degrees Celsius/minute to a temperature endpoint in the target tissue. The temperature endpoint of an embodiment is approximately in the range of 55 degrees Celsius to 110 degrees Celsius, but is not so limited. The use of an appropriate rise in tissue temperature around an electrode results in release of the highly conductive fluid inside cells of the target tissue. This fluid release lowers the impedance around the electrode helping to prevent charring and allowing the continued (or increasing) flow of energy to the target tissue. This release is caused by the thermal damage to the cell wall. If the energy rise is too quick, the fluid will be quickly boiled or flashed off; this results in no significant benefit and helps to increase the tendency for tissue charring and a loss of ability to deliver energy to the target tissue.

The third type of procedure varies the application of energy to the target tissue volume in accordance with impedance information or feedback parameters of the tissue in combination with elapsed time. Generally, this type of procedure applies power to the target tissue according to pre-established time schedules and in accordance with changes in impedance and an amount of electrode engagement with the target tissue (engaged surface area of electrodes is a function of electrode size and electrode deployment depth).

Figure 16:
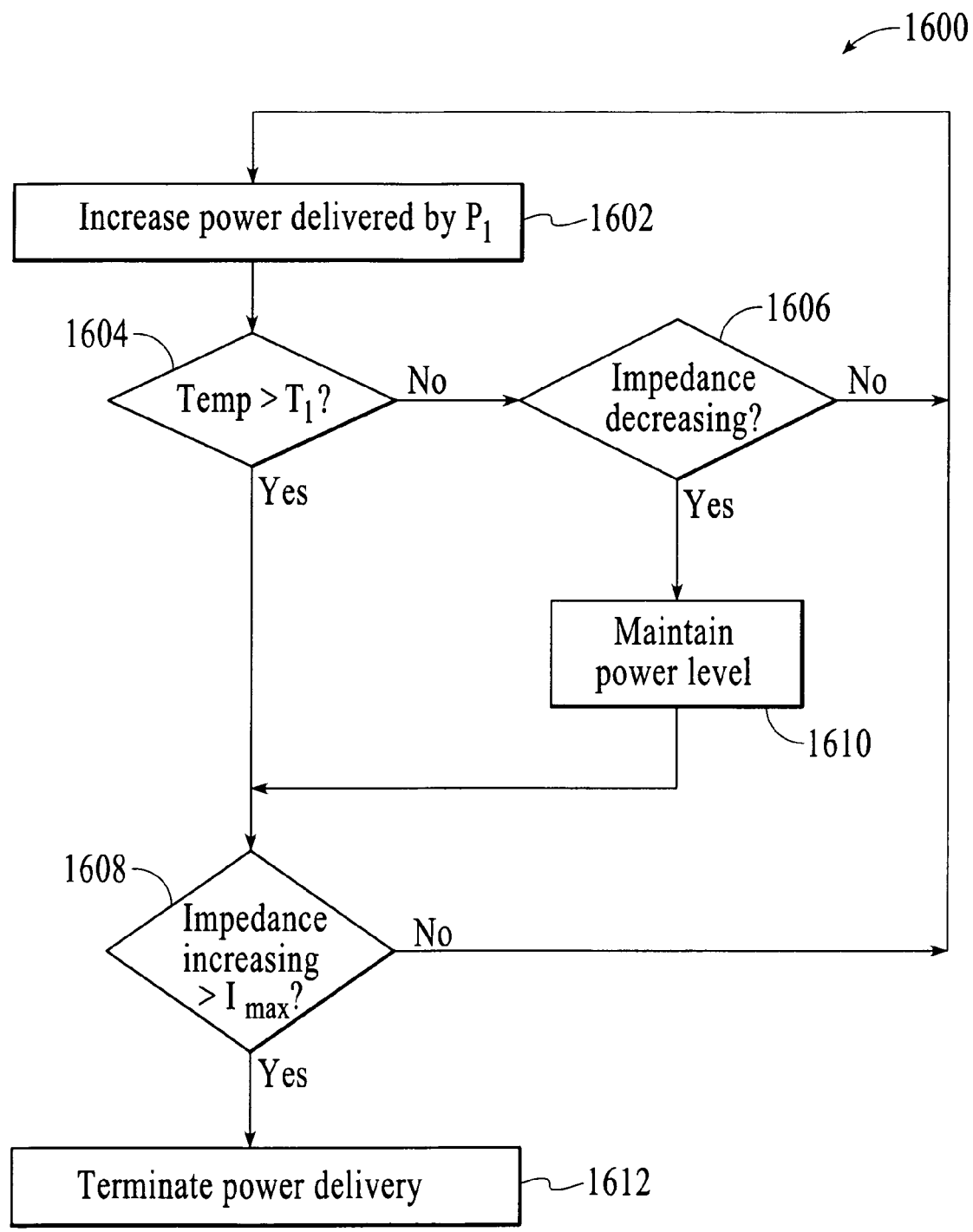
FIG. 16 is a flow diagram for controlling tissue ablation in accordance with impedance and time parameters, under an embodiment.

FIG. 16 is a flow diagram 1600 for controlling tissue ablation in accordance with impedance and time parameters, under an embodiment. Following placement of the electrodes in the target tissue, the user increases the power delivered to the target tissue by an amount $P_1$, at block 1602, where $P_1$ is approximately in the range 0.1 W/sec to 10 W/sec. A determination is made whether the elapsed time is greater than $T_1$, at block 1604, where $T_1$ is approximately in the range 1 second to 100 seconds.

When the elapsed time exceeds $T_1$, a determination is made whether an impedance of the target tissue is greater than an amount $I_{max}$, at block 1608, where $I_{max}$ is approximately in the range 1 Ohm to 200 Ohms. When the impedance exceeds $I_{max}$, the application of power to the target tissue is terminated, at block 1612; otherwise, operation continues at block 1602 as described above.

When the elapsed time does not exceed $T_1$, as determined at block 1604, a determination is made whether the impedance of the target tissue is decreasing, at block 1606. If the impedance is not decreasing, then operation continues at block 1602, as described above. If the impedance is increasing, then the application of power to the target tissue is maintained, at block 1610, and operation continues at block 1608 where a determination is made as to whether impedance of the target tissue is greater than an amount $I_{max}$. When the impedance exceeds $I_{max}$, the application of power to the target tissue is terminated, at block 1612; otherwise, operation continues at block 1602 as described above.

An example procedure that controls tissue ablation in accordance with impedance parameters, as described above, uses the following parameter values: $P_1$ is approximately 2 W/sec; $T_1$ is approximately 15 seconds; and $I_{max}$ is approximately 50 Ohms. These parameters are examples only and do not limit the embodiments described herein.

The fourth type of procedure varies the application of power to the target tissue volume in accordance with impedance information or feedback parameters of the tissue. Generally, this type of procedure applies power to the target tissue in accordance with changes in impedance and an amount of electrode engagement with the target tissue (engaged surface area of electrodes is a function of electrode size and electrode deployment depth). As an example, power is applied in one embodiment until the impedance of the target tissue begins to drop. As the impedance begins to drop, the power level is stabilized at an approximately constant level until the impedance stabilizes. Once the impedance stabilizes, the power level is increased to a predetermined level and held until the impedance begins to increase. As the impedance begins to increase, the power level can be gradually decreased in order to maintain or prolong the duration of the impedance rise.

As another example, power is applied until the impedance of the target tissue begins to drop. As the impedance begins to drop, the power level is stabilized at an approximately constant level until the impedance stabilizes. Once the impedance stabilizes, the power level is gradually increased until such time as the impedance begins to increase. A maximum power level can be specified, but the embodiment is not so limited. As the impedance begins to increase, the power level can be gradually decreased in order to maintain or prolong the duration of the impedance rise.

Figure 17:
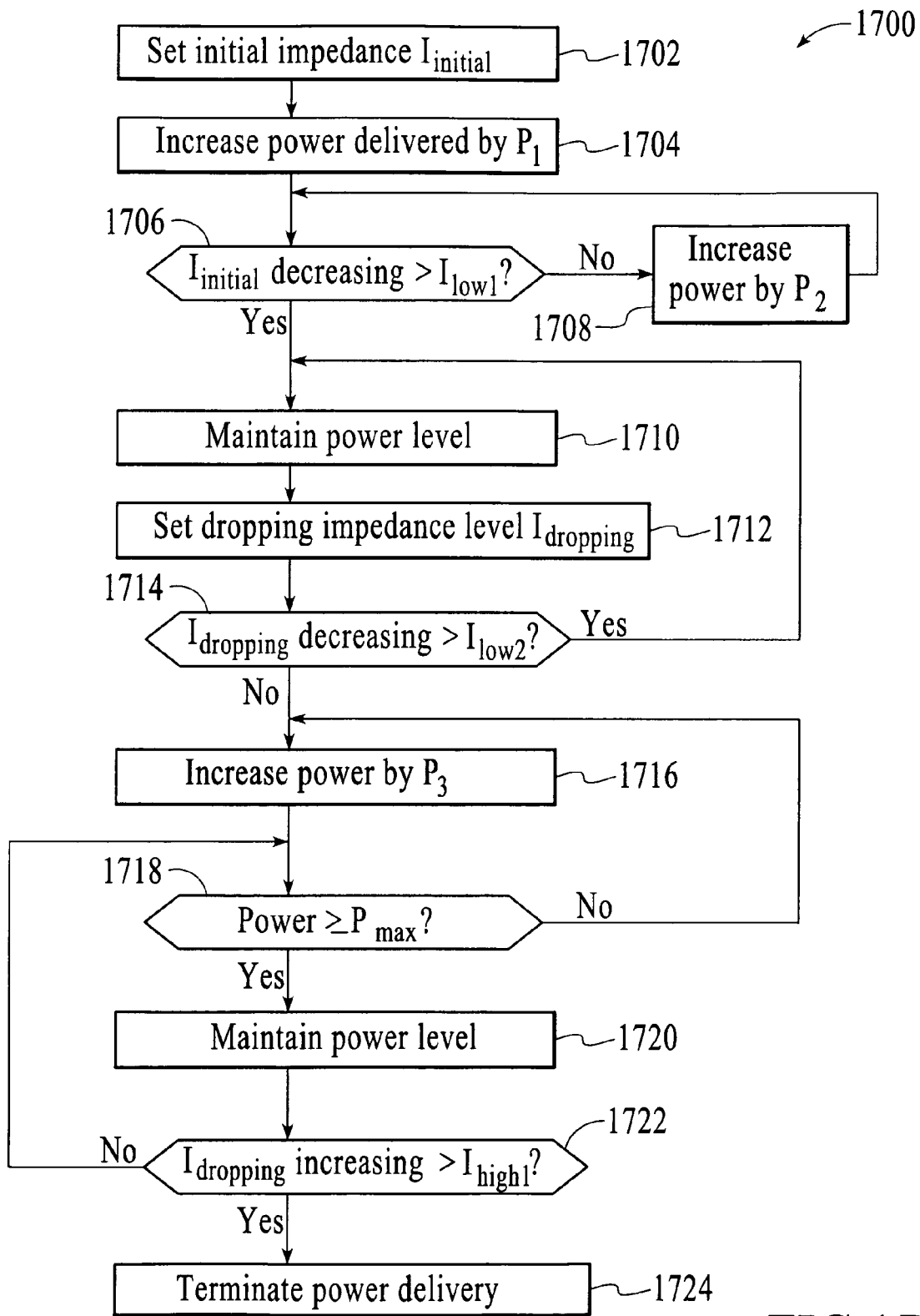
FIG. 17 is a flow diagram for controlling tissue ablation in accordance with impedance parameters, under an embodiment.

FIG. 17 is a flow diagram 1700 for controlling tissue ablation in accordance with impedance parameters, under an embodiment. Following placement of the electrodes in the target tissue, an initial impedance level $I_{initial}$ is set, at block 1702, where $I_{initial}$ is selected or determined according to the tissue type of the target tissue. The power delivered to the target tissue is then increased by an amount $P_1$, at block 1704, where $P_1$ is approximately in the range 0.1 W/sec to 10 W/sec. A determination is made whether the initial impedance level $I_{initial}$ has decreased more than an amount $I_{low1}$, at block 1706, where $I_{low1}$ is approximately in the range 0.1 Ohms to 5 Ohms. If the initial impedance level $I_{initial}$ has not decreased more than $I_{low1}$, the power delivered to the target tissue is increased by an amount $P_2$, at block 1708, where $P_2$ is approximately in the range 0.1 W/sec to 10 W/sec, and operation continues at block 1706 as described above.

If the initial impedance level $I_{initial}$ has decreased more than $I_{low1}$, the power delivered to the target tissue is stabilized and maintained at the current level, at block 1710. The decreased impedance of the target tissue is set and defined as a value $I_{dropping}$, at block 1712. The impedance level $I_{dropping}$ is then monitored for decreases that exceed impedance level $I_{low2}$, at block 1714, where $I_{low2}$ is approximately in the range 1 Ohm to 20 Ohms. If the impedance level $I_{dropping}$ has decreased more than $I_{low2}$, operation continues at block 1710, where the power delivered to the target tissue is maintained and operation continues as described above.

If the impedance level $I_{dropping}$ has not decreased more than $I_{low2}$, the power delivered to the target tissue is increased by an amount $P_3$, at block 1716, where $P_3$ is approximately in the range 0.1 W/sec to 10 W/sec. A determination is then made whether the amount of power delivered to the target tissue is equal to or greater than an amount $P_{max}$, at block 1718. The power level $P_{max}$ of an embodiment is determined from a lookup table in response to at least one parameter that includes target tissue type, initial impedance level $I_{initial}$, electrode size, and electrode deployment depth, but is not so limited. Alternatively, $P_{max}$ is pre-specified and preset in accordance with at least one parameter that includes target tissue type, initial impedance level $I_{initial}$, electrode size, and electrode deployment depth, but is not so limited. If the current power level is less than $P_{max}$ then the power delivered to the target tissue is increased by an amount $P_3$, at block 1716, and operation continues as described above.

If the power level is equal to or greater than $P_{max}$, at block 1718, the power level is maintained, at block 1720. The impedance level $I_{dropping}$ is then monitored for increases that exceed an amount $I_{high1}$, at block 1722. Impedance level $I_{high1}$ of an embodiment is approximately equal to or greater than two times impedance level $I_{initial}$, but is not so limited. If the change in impedance level $I_{dropping}$ does not exceed $I_{high1}$, a determination is made whether the level of power delivered to the target tissue is equal to or greater than an amount $P_{max}$, at block 1718, and operation continues as described above. If the change in impedance level $I_{dropping}$ exceeds $I_{high1}$, however, the application of power to the target tissue is terminated, at block 1724.

An example procedure that controls tissue ablation in accordance with impedance parameters, as described above, uses the following parameter values: $P_1$ is approximately 2 W/sec; $P_2$ is approximately 4 W/sec; $I_{low1}$ is approximately 1 Ohm; and $I_{low2}$ is approximately 1 Ohm. Alternatively, power levels $P_1$, $P_2$, and $P_3$ can be equal, but are not so limited. These parameters are examples only and do not limit the embodiments described herein.

Figure 18:
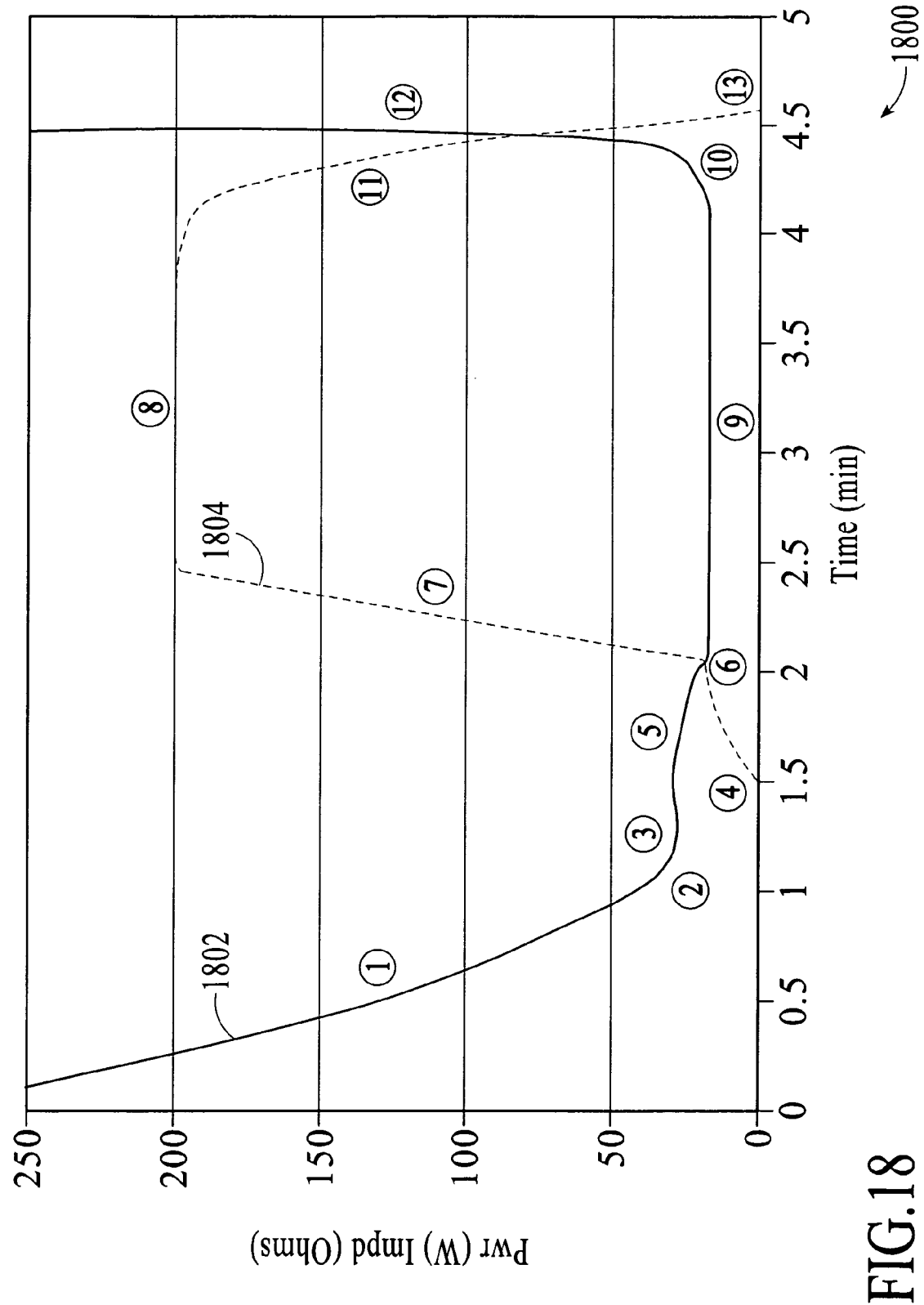
FIG. 18 is a plot of impedance and power versus time for use in controlling tissue ablation, under an embodiment.

FIG. 18 is a plot 1800 of impedance (Impd (Ohms)) 1802 and power (Pwr (W)) 1804 (y-axis) versus time (Time (min)) (x-axis) for use in controlling tissue ablation, under an embodiment. In the following description, the impedance curve 1802 includes Regions 1, 2, 3, 5, 6, 9, 10, and 12, while the power curve 1804 includes Regions 4, 7, 8, 11, and 13. This plot 1800 generally represents the impedance 1802 and power 1804 during a tissue ablation procedure using the tissue ablation system of an embodiment under impedance control. This plot 1800 can generally be used in at least one of manual, automatic, and combination automatic/manual control of the tissue ablation system of an embodiment. This plot 1800 is an example only and does not limit the embodiments described herein.

The plot 1800 was derived using an electrode deployment depth in the target tissue of approximately four to five centimeters, but is not so limited. A decrease in the electrode deployment depth, for example, would shift the impedance 1802 curve up and the power 1804 curve down relative to values on the y-axis. Further, different types of target tissue can shift the impedance 1802 and power 1804 curves up or down. Moreover, electrodes of different sizes can change a shape of the impedance curve 1802 where, generally, larger electrodes result in more gradual changes in the impedance curve relative to smaller electrodes.

Procedures that use the tissue ablation system of an embodiment begin with placement/deployment of the electrodes into the target tissue by the user. Using standard surgical techniques, the user determines the appropriate resection plane to be used. All electrodes of the device are retracted, and the device is placed in contact with the patient such that all electrodes are properly positioned for deployment into the intended tissue. The electrodes are then deployed into the target tissue using imaging guidance as appropriate. Region 1 of the plot 1800 generally represents the decreasing impedance resulting from electrode placement/deployment in the target tissue. Region 2 generally represents the impedance as it stabilizes during/after final electrode placement in the target tissue. Region 3 generally represents stable impedance following electrode placement in the target tissue.

Following placement of the electrodes in the target tissue and stabilization of the impedance, power is applied to the target tissue via the deployed electrodes as described above. Region 4 generally represents the point at which the tissue ablation system applies power to the target tissue. Region 5 generally represents the decreasing impedance in the target tissue that arises as a result of the application of power. The decreasing impedance results as the application of power causes cell membranes in the target tissue to rupture and release conductive fluid into the area of the electrodes. Region 6 generally represents stabilized impedance in the target tissue following the initial application of power by the tissue ablation system.

Once the impedance has stabilized in the target tissue, the tissue ablation system increases the power applied to the target tissue. The power can be increased according to any number of procedures, including increasing in step-wise fashion, increasing linearly to a pre-specified maximum level, increasing in an exponential fashion, and increasing until a pre-specified temperature is reached in the target tissue, to name a few. Region 7 generally represents an increase in power applied to the target tissue, and Region 8 generally represents a maximum power level to which the power is increased. Region 9 generally represents stabilized impedance in the target tissue during/following the increased application of power by the tissue ablation system.

Desiccation of the target tissue occurs as a result of the power applied to the tissue (Regions 7 and 8 of the plot). Desiccation of the target tissue generally results in an increase in the impedance of the target tissue, where the rate of increase in impedance is controlled in response to the level of applied power. Region 10 generally represents the onset of increasing impedance in the target tissue as a result of tissue desiccation. Region 11 generally represents a reduction rate of the power applied to the target tissue in response to the increasing impedance, while area 12 generally represents the corresponding rate of increase of the impedance in the target tissue.

The tissue ablation system, under automatic and/or manual control, reduces the power applied to the target tissue at any of a number of rates in order to control the rate at which the impedance rises. For example, increasing the rate at which the power is reduced (increasing slope of Region 11) results in a slower increase in the impedance (decreasing slope of Region 12). Likewise, decreasing the rate at which the power is reduced (decreasing slope of Region 11) results in a faster increase in the impedance (increasing slope of Region 12). Rates of power reduction are specified as appropriate to a tissue type of the target tissue and/or a user, but are not so limited.

Region 13 generally represents termination of the application of power to the target tissue and, therefore, termination of the ablation procedure.

Turning to the fifth type of procedure, this procedure varies the application of energy to the target tissue volume in accordance with temperature and impedance information or feedback parameters of the target tissue. Generally, this type of procedure applies power to the target tissue in accordance with changes in temperature and impedance in the target tissue. The impedance changes relate to an amount of electrode engagement with the target tissue (engaged surface area of electrodes is a function of electrode size and electrode deployment depth), but are not so limited.

As an example, power is applied in one embodiment until the impedance of the target tissue begins to decrease. As the impedance decreases, the power level is stabilized at an approximately constant level until the impedance stabilizes. Once the impedance stabilizes, the power level is increased according to a predetermined slope. When a pre-specified target temperature is reached in the target tissue, the power level is altered so as to maintain the target temperature until such time as the impedance increases to a pre-specified target impedance. In an alternative procedure, when a pre-specified target temperature is reached in the target tissue, the power level is altered so as to maintain the target temperature until such time as the impedance increases at a pre-specified rate of increase.

The tissue ablation system and associated processes described above can include other components in a variety of combinations. In addition to the display and controller described above, for example, a stereotactic frame or frameless navigator system may be used to direct and place the energy director guide/electrodes. Various guide tubes, templates, holding apparatus, arc systems, and spatial digitizers can also be used to assist in placement of the electrodes in the target tissue. Imaging modalities such as CT, MRI, ultrasound and the like can be used before, during, or after placement of the electrodes and/or creation of the ablation volume.

In addition to including numerous types and combinations of components, there are many alternative embodiments of the tissue ablation system components described above. Some of these alternatives include alternative embodiments of the energy director guide and the electrodes, as described below.

The energy director guide of one alternative embodiment includes a soft conformal bottom element that forms a conformal surface between the target tissue and the energy director guide. The conformal element takes on the shape of the surface of the underlying target tissue. Conformal bottom elements can be constructed from a variety of materials including silicone, biocompatible foam rubbers, and urethanes. Conformal bottom elements can also be formed with the use of inflated members.

The energy director guide of various alternative embodiments may take on a variety of shapes including, but not limited to, semi-circular, arcs, and angles. Many other shapes will be recognized by those skilled in the art.

Figure 19:
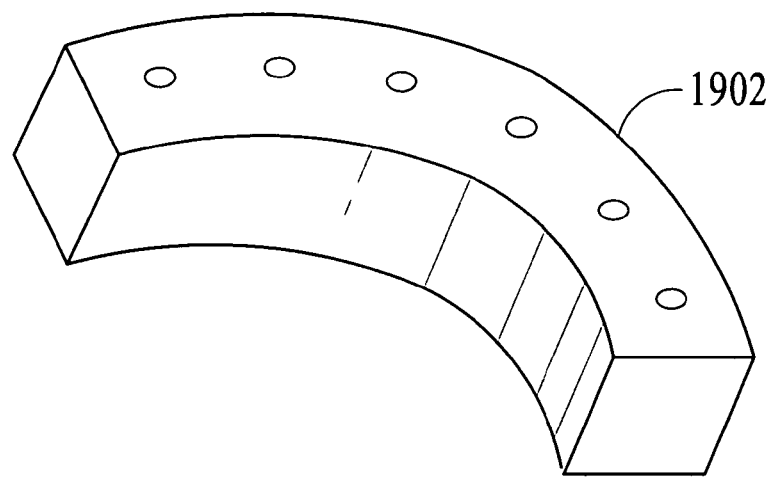
FIG. 19 shows a flexible or semi-flexible guide having flexibility in two planes, under an alternative embodiment.
Figure 20:
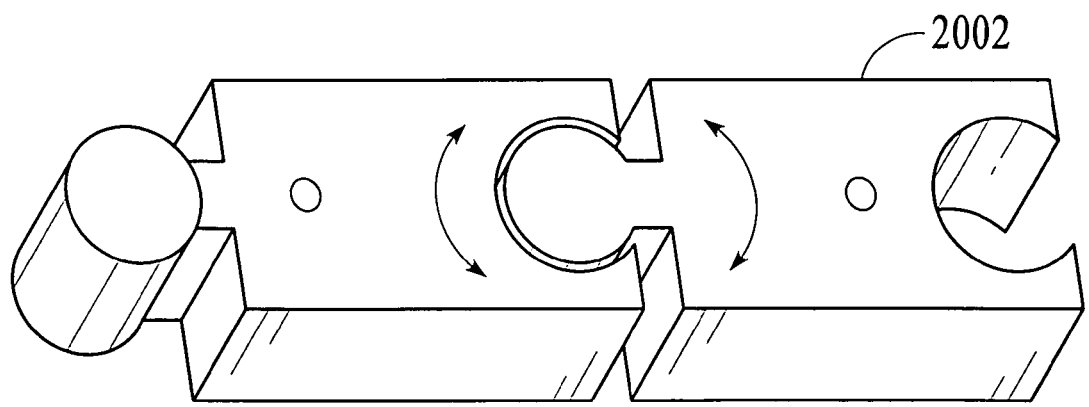
FIG. 20 shows a flexible or semi-flexible guide having flexibility in one plane, under another alternative embodiment.

FIG. 19 shows a flexible or semi-flexible guide 1902, under an embodiment. This flexible guide 1902 provides flexibility in two planes. FIG. 20 shows a flexible or semi-flexible guide 2002, under another alternative embodiment, that provides flexibility in one plane. These guides 1902 and 2002, while being configured to secure and couple power to the electrodes as described above with reference to FIGS. 2, 3, 8, 9, and 10, permit the user to alter the guide within limits to create a desired shape which, in turn, allows the resulting coagulation plane to match the desired outcome or avoid critical anatomical structures. Note that desired shapes including curved portions are formed from a series of coagulation planes having various dimensions, but the embodiment is not so limited.

These guides can be flexible or semi-flexible in a single or multiple planes. In a single plane, the guide can be shaped to the tissue targeted below the guide. With a second plane of flexibility, the guide can be used to contour to the shape of the surface or as necessary for location of the operative site.

Figure 21:
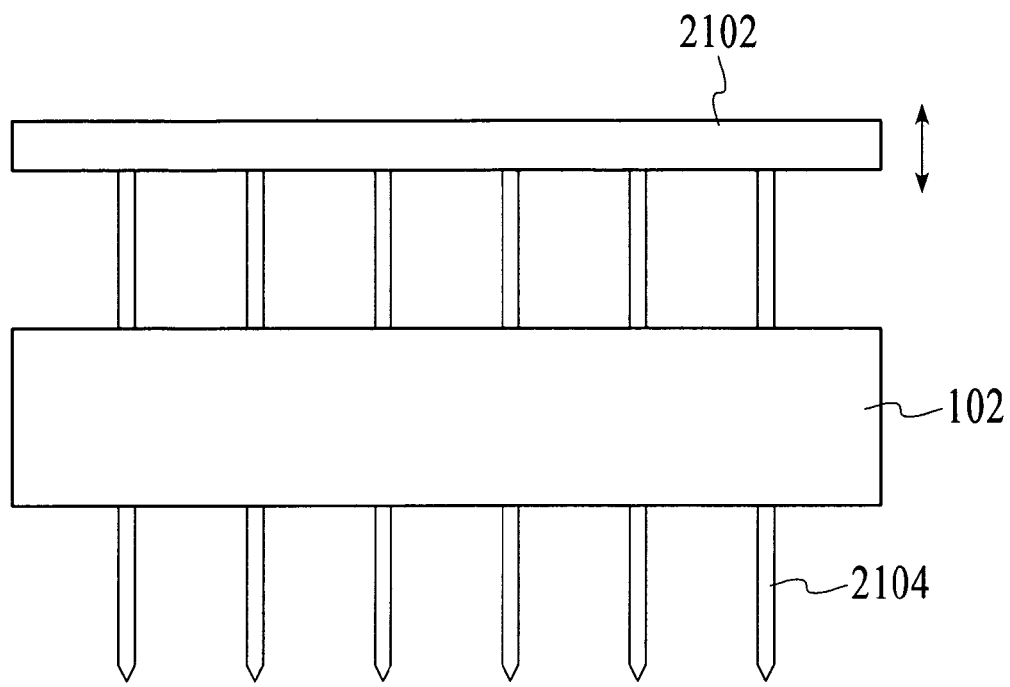
FIG. 21 is an energy director array including a joining member that provides for simultaneous insertion or retraction of energy directors into target tissue, under an embodiment.

FIG. 21 is an energy director array including a joining member 2102 that provides for simultaneous insertion or retraction of energy directors 2104 into target tissue, under an embodiment. The energy directors are connected to the joining member 2102 to allow for the simultaneous insertion or retraction of all energy directors 2104 via the energy director guide 102. As one example, all energy directors 2104 can be of the same length, thereby allowing the simultaneous insertion of all energy directors 2104 to a desired depth within the tissue. This is of benefit when a full thickness ablation plane is desired, there are no anatomical structures that would be contraindicated for the energy directors, and ease of use is important.

Figure 22:
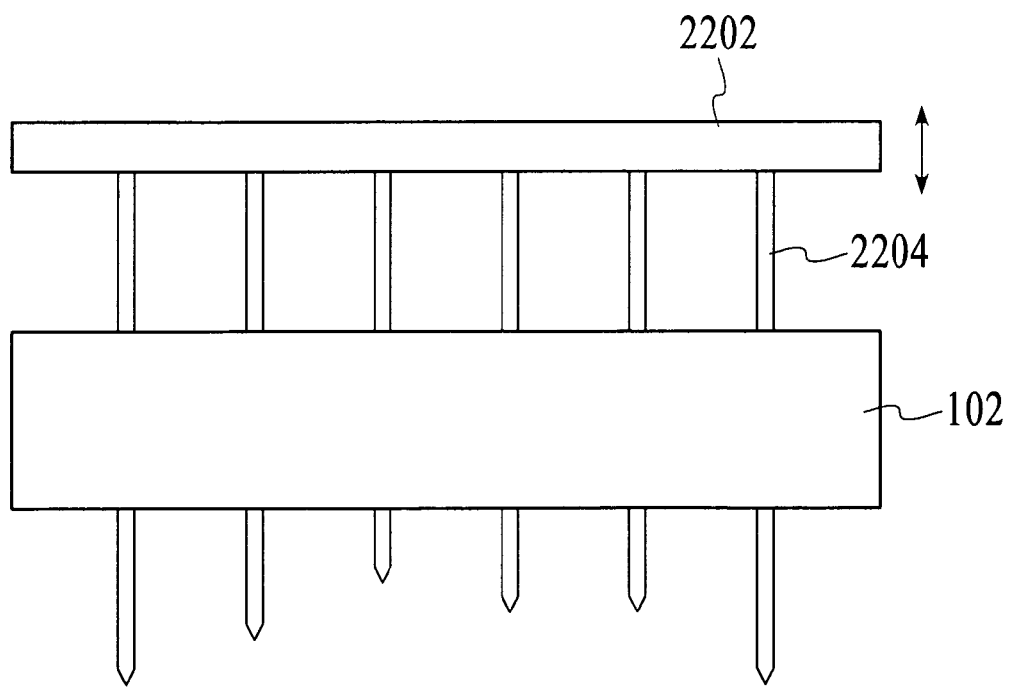
FIG. 22 is an energy director array including a joining member connected to energy directors, under an alternative embodiment.

FIG. 22 is an energy director array including a joining member 2202 connected to energy directors 2204, under an alternative embodiment. Select energy directors 2204 have non-uniform lengths as they are tailored to match the thickness and shape of the target tissue or organ and/or to avoid critical anatomical structures. The joining member 2202, therefore, supports the simultaneous insertion and withdrawal of all energy directors regardless of length while also supporting the avoidance of critical anatomical structures by the energy directors 2204.

The energy directors of an embodiment can be used with a variety of housings that enclose the energy directors prior to deployment into target tissue. Use of the housing minimizes unintentional deployment of the energy directors and reduces the potential for injury of a user or patient by the energy directors.

Many different types of energy directors can be used with the tissue ablation system of an embodiment. Descriptions follow of some example energy directors, but the embodiment is not so limited.

Figure 23:
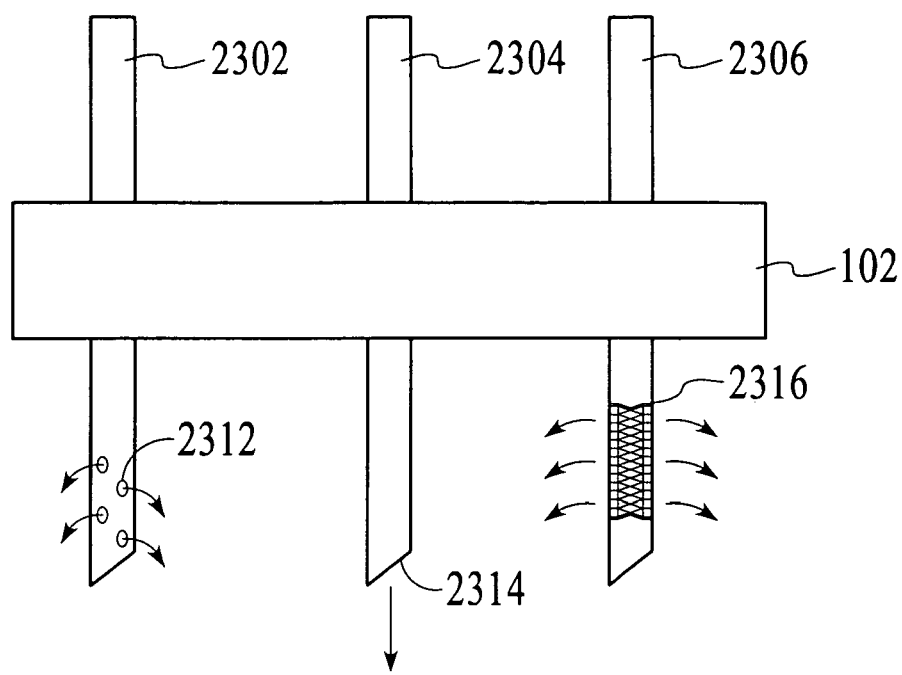
FIG. 23 shows energy directors supporting delivery of various agents into the target tissue, under an embodiment.

FIG. 23 shows energy directors 2302, 2304, and 2306 supporting delivery of various agents into the target tissue, under an embodiment. One type of energy director 2302 supports delivery of agents through a lumen in the energy director and apertures 2312 around the outer surface of the energy director 2302.

Another type of energy director 2304 supports delivery of agents through a lumen in the energy director and at least one aperture 2314 in the distal end of the energy director 2304. Yet another type of energy director 2306 supports delivery of agents through a lumen in the energy director in communication with a porous material 2316 around the outer surface of the energy director 2306.

The energy directors 2302, 2304, and 2306 support deliver of agents including, but not limited to, contrast agents used to better visualizes the detailed anatomy, sclerotic agents to help decrease the overall circulation in the target region, and chemotherapy agents for use as an adjunctive therapy. Still another example agent is a hyper- or hypo-tonic solution used to create a wet electrode.

Figure 24:
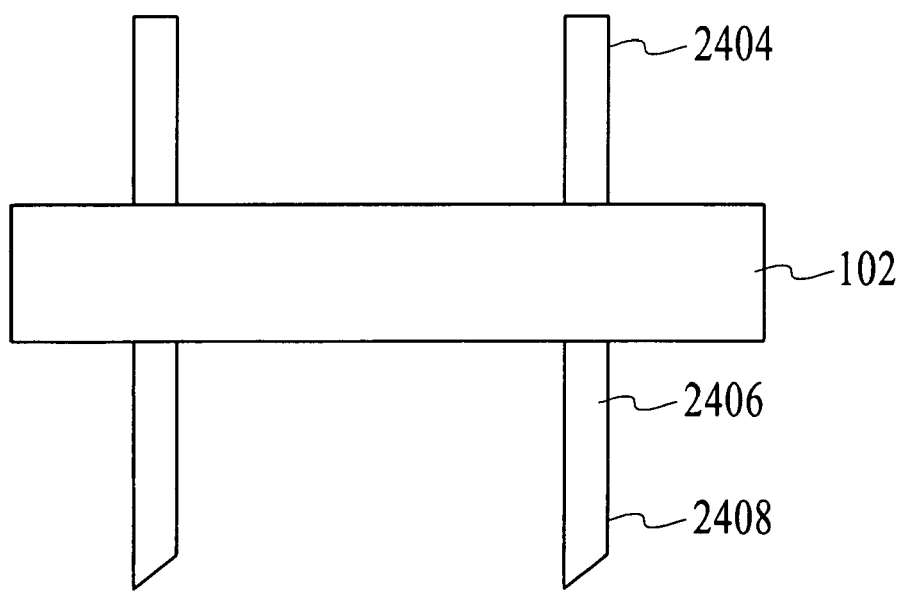
FIG. 24 shows energy directors that capacitively couple to target tissue, under an embodiment.

FIG. 24 shows energy directors 2404 that capacitively couple to target tissue, under an embodiment. In this embodiment the energy directors 2404 are fully, or near-fully insulated. An example of this configuration includes one or more conducting cores 2406 suitable for conducting energy, where the conducting core 2406 is fully or near fully insulated with an appropriate dielectric material 2408, coating, or sleeve. The thickness of coating 2408 varies according to the dielectric properties of the material used as the electrical insulator. Coating thicknesses of the various embodiments range from approximately 0.00005 inch to 0.001 inch, but are not so limited. In this configuration, the energy directors 2404 induce an energy flow into the target tissue. When appropriately applied, this energy would then cause the target tissue to heat and coagulate, as described above. The use of capacitive coupling in this form can increase the relatively low electrical impedance that results when several energy directors 2404 are used at a relatively close spacing.

The tissue ablation system of an embodiment includes one or more energy directors that support temperature monitoring within and/or around the target tissue. The temperature monitoring supported by the energy directors supports the real-time evaluation of an ablation procedure both outside and within the effected tissue zone. An example of this could be one or more thermocouples arranged in a configuration suitable for placement within the tissue, for example on and/or within an associated energy director, wherein the thermocouples couple to temperature monitoring equipment known in the art.

In generating coagulative ablation, the tissue ablation system and associated procedures of an embodiment deliver energy that results in tissue core temperatures approximately in the range between 65 degrees Celsius and 80 degrees Celsius in the coldest portions of the target tissue volume. The coldest portions of the target tissue volume are typically those areas that are the most distant from the energy directors or are thermally shielded from the effect of the energy directors by other anatomical structures.

Likewise, the tissue ablation system and associated procedures deliver energy that results in tissue core temperatures approximately in the range between 85 degrees Celsius and 105 degrees Celsius in the warmest portions of the target tissue volume. At temperatures below this, procedural times may be unnecessarily extended. At temperatures above this, instability may result due to the superficial charring caused by the excessive tissue heating. As noted herein, these conditions can be further mitigated with the use of other factors such has hypertonic agents. In particular, a continuous infusion of a 0.9% to 8% saline solution at an approximate rate of between 0.01 cc/min to 0.5 cc/min will aid in preventing tissue charring.

The temperature monitoring energy director provides the ability to control the energy delivered to the target tissue by controlling the energy with the use of a closed- or open-loop temperature feedback system. As such, optimum energy delivery can be achieved, thereby avoiding over delivery or under delivery of energy. Over delivery of energy can create superficially charred tissue resulting in a reduction or inability to deliver energy and an incomplete ablation. Under delivery of energy could significantly increase the procedural duration or even prevent the ability to complete the procedure. By controlling the transfer of energy to the target tissue in this manner, and by using non-stick surfaces such as fluoropolymers like polypropelene and parylene on the energy directors, charring can be minimized to produce optimal energy delivery and tissue ablation. In addition, the use of temperature monitoring also provides evidence and feedback as to the completion of the procedure, as described above.

As described above, the energy director guide of an embodiment configures the energy directors to provide approximately uniform power or energy distribution through the target tissue volume. Alternative embodiments of the tissue ablation system support the application of non-uniform energy distribution via either linear or non-linearly spaced arrays. This configuration monitors a parameter such as temperature, power, or impedance and, in response, controls the delivered energy to maintain the parameter(s) within a desired target range. By using individual energy channels for each bipolar pair, the energy can easily be altered as needed. For example, with a temperature goal of 80 degrees Celsius after initial ramps of 1.5 minutes to full power, or a predetermined maximum power, the time-temperature slopes are evaluated for each zone based on a predetermined ramp (approximately in the range of 50-80 degrees Celsius/minute). Based on the temperature ramp the power is altered to better match the desired rate.

Note that patent and procedure selection is the responsibility of the medical professional user and the outcome is dependent on many variables, including patient anatomy, pathology, and surgical techniques. Use of the tissue ablation system and methods described herein for thermal coagulation necrosis of soft tissues as an aid during tissue resection can result in localized elevated temperatures that can cause thermal injury to the skin. In addition, tissue or organs adjacent to the tissue being ablated may be injured thermally. To minimize the potential for thermal injury to the skin or adjacent tissues, temperature-modifying measures can be initiated at the physician's discretion. These may include applying a sterile ice pack or saline-moistened gauze to cool and/or separate tissues, but are not so limited.

A tissue ablation system described above comprises: an energy source; two or more pairs of bipolar energy directors configured for insertion into a volume of biological tissue; and an energy director guide that configures the energy directors to generate at least one plane of coagulated tissue in the volume of tissue by coupling energy from the energy source to the volume of tissue, wherein the energy director configuration results in approximately uniform energy distribution through the tissue volume; wherein the guide includes a series of channels that receive the energy directors in an alternating polarity series, wherein spacing among the channels varies according to a number of pairs of energy directors received in the energy director guide so that relative spacing among the center-most channels is largest and relative spacing among the end-most channels is smallest; and wherein the guide independently couples the energy source to each of the energy directors.

The tissue ablation system of an embodiment comprises an energy source that includes a radio frequency generator.

The energy director guide of an embodiment further secures a selected depth position of the energy directors in the tissue volume.

The two or more pairs of bipolar energy directors of an embodiment include three pairs of bipolar energy directors. Alternatively, the two or more pairs of bipolar energy directors of an embodiment include four pairs of bipolar energy directors.

The energy directors of an embodiment further include at least one component selected from among temperature sensors, thermocouples, infusion components, and optical tissue monitors.

The tissue ablation system of an embodiment further comprises at least one controller coupled among the energy source and the bipolar energy directors, wherein the controller supports automatic control of energy delivery to each of the bipolar energy directors.

The energy directors of an embodiment are inserted to independently variable depths in the volume of biological tissue.

The energy directors of an embodiment are internally cooled.

The tissue ablation system of an embodiment further comprises at least one housing, wherein the housing includes the energy directors and is configured to couple to the energy director guide, wherein the energy directors are deployed from the housing and inserted into the volume of biological tissue.

The uniform energy distribution of an embodiment includes uniform current density.

The alternating polarity series of an embodiment includes at least one electrode of a positive polarity in series with at least one electrode of a negative polarity.

A system described above for generating at least one plane of coagulated tissue in a volume of biological tissue comprises at least one guide including a series of channels that configure two or more sets of bipolar electrodes in an alternating polarity series, wherein spacing among the channels varies according to a total number of bipolar electrodes received in the guide so that relative spacing among the center-most channels is largest and relative spacing among the end-most channels is smallest, wherein the guide secures a selected position of each of the electrodes in the target biological tissue and couples each bipolar electrode to at least one energy source.

A method for use with the tissue ablation systems described above for generating at least one plane of coagulated tissue in biological tissue, comprises: positioning an electrode guide on a surface of a biological tissue region that includes a target tissue volume, wherein the electrode guide includes a series of channels that configure two or more pairs of bipolar electrodes in an alternating polarity series, wherein spacing among the channels varies according to a total number of bipolar electrodes received in the guide so that relative spacing among the center-most channels is largest and relative spacing among the end-most channels is smallest; securing the bipolar electrodes at a selected depth in the target tissue volume using the electrode guide; coupling at least one energy source to the bipolar electrodes using the electrode guide and providing approximately uniform energy distribution through the target tissue volume; and generating the at least one plane of coagulated tissue in the target tissue volume. The method for use with tissue ablation systems of an embodiment further comprises infusing a solution into the target tissue volume via at least one of the bipolar electrodes, wherein the solution is at least one of a hyper-tonic solution, a hypo-tonic solution, a contrast agent, a sclerotic agent, and a chemotherapy agent.

A method for use with the tissue ablation systems described above for generating a plane of coagulated tissue in biological tissue, comprises: positioning an electrode guide in proximity to a target tissue volume; inserting two or more pairs of bipolar electrodes into the target tissue volume in a series of alternating polarity via the electrode guide; securing the bipolar electrodes at a selected depth in the target tissue volume using components of the electrode guide; coupling at least one energy source to the target tissue volume via the bipolar electrodes; controlling energy delivery to effect approximately uniform energy distribution through the target tissue volume, wherein a target temperature in the target tissue volume is greater than a temperature approximately in the range of 55 degrees Celsius to 60 degrees Celsius; and generating the plane of coagulated tissue in the target tissue volume. The method further comprises measuring the target temperature at one or more of the electrodes. The method further comprises measuring the target temperature at one or more points in the target tissue volume.

A tissue ablation apparatus described above for use in a resection procedure of tissue within a mammalian body, comprises: a support body having a first and second end portions and a surface extending between the first and second end portions; and a plurality of at least first, second and third elongate radio frequency electrodes carried by the support body and extending from the surface in spaced-apart positions between the first and second end portions, the first and second electrodes being spaced apart by a first distance and the second and third electrodes being spaced apart by a second distance different than the first distance, the first and second distances being chosen so that when the first, second and third electrodes are disposed in the tissue the energy distribution between the first and second electrodes and the energy distribution between the second and third electrodes are approximately uniform.

The first, second and third electrodes of an embodiment are parallel.

The first, second and third electrodes of an embodiment are needle electrodes.

The tissue ablation apparatus described above for use in a resection procedure of tissue within a mammalian body further comprises a fourth elongate radio frequency electrode spaced from the third electrode by a third distance different from the first and second distances, the third distance being chosen so that when the second, third and fourth electrodes are disposed in the tissue the energy distribution between the second and third electrodes and the energy distribution between the third and fourth electrodes are approximately uniform.

The tissue ablation apparatus of an embodiment described above for use in a resection procedure of tissue within a mammalian body further comprises a radio frequency generator coupled to the first and second electrodes for supplying a first potential to the first electrode and a second potential to the second electrode.

The tissue ablation apparatus of an embodiment described above for use in a resection procedure of tissue within a mammalian body further comprises a radio frequency generator coupled to the radio frequency electrodes for supplying a first potential to the first and second electrodes and a second potential to the third and fourth electrodes.

A method for use with the tissue ablation systems described above for resecting a portion of a target organ within a mammalian body using a support body having a first and second end portions and a surface extending between the first and second end portions and a plurality of electrodes extending from the surface and spaced sequentially between the first and second end portions, comprises: positioning the electrodes in the vicinity of the target organ; extending the electrodes into the target organ; supplying a first potential of radio frequency energy to a first group of the plurality of electrodes and a second potential of radio frequency energy to a second group of the plurality of electrodes so that radio frequency energy travels between the first and second groups of electrodes and thus forms a wall of ablated tissue in the target organ; and incising the target organ in the vicinity of the wall of ablated tissue to resect the portion of the target organ.

The method for resecting a portion of a target organ further comprises estimating a transverse dimension of the target organ and sizing the electrodes as a function of the transverse dimension to prevent the electrodes from extending beyond the target organ when the surface is substantially flush with the target organ.

The method for resecting a portion of a target organ further comprises separating the target organ from an adjacent organ to prevent the electrodes from piercing the adjacent organ when the electrodes are extended into the target organ. The separation of an embodiment is achieved by placing a shield between the target organ and the adjacent organ to protect the adjacent organ from the electrodes.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," and words of similar import, when used in this application, shall refer to this application as a whole and not to any particular portions of this application. When the word "or" is used in reference to a list of two or more items, that word covers all of the following interpretations of the word: any of the items in the list, all of the items in the list and any combination of the items in the list.

The above description of illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings of the invention provided herein can be applied to other ablation systems, resection systems, and medical devices, not only for the tissue ablation system described above.

The elements and acts of the various embodiments described above can be combined to provide further embodiments. These and other changes can be made to the invention in light of the above detailed description.

All of the above references and United States patent applications are incorporated herein by reference. Aspects of the invention can be modified, if necessary, to employ the systems, functions and concepts of the various patents and applications described above to provide yet further embodiments of the invention.

In general, in the following claims, the terms used should not be construed to limit the invention to the specific embodiments disclosed in the specification and the claims, but should be construed to include all processing systems that operate under the claims to provide a method for compressing and decompressing data files or streams. Accordingly, the invention is not limited by the disclosure, but instead the scope of the invention is to be determined entirely by the claims.

While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

We claim:

1. A method for performing thermal coagulation necrosis of biological tissue, comprising:
   configuring an electrode array that provides a balanced energy density in at least one target tissue volume using two or more pair of bipolar electrodes having a configuration that includes at least one of irregular spacing between one or more pairs of the electrodes and one or more electrode diameters;

deploying each electrode of the electrode array at a selected depth in the target tissue volume using the configuration;

delivering the balanced energy to the target tissue volume from at least one radio frequency (RF) power source via the electrodes and controlling the delivery in response to at least one of elapsed time of the delivery, a temperature of the target tissue volume, and an impedance of the target tissue volume; and generating at least one plane of coagulated tissue.

2. The method of claim 1, further comprising positioning an electrode guide on a surface of a biological tissue region that includes the target tissue volume, wherein the electrode guide includes a series of channels that position the electrodes in accordance with the configuration.

3. The method of claim 1, wherein spacing among the electrodes varies according to at least one of a total number of electrodes in the electrode array, the electrode diameters, and the selected deployment depth of each electrode in the target tissue volume.

4. The method of claim 1, wherein spacing among the center-most electrodes of the array is larger relative to spacing among the end-most electrodes.

5. The method of claim 1, wherein configuring the electrode array further comprises forming a linear electrode array that includes a first set of electrodes on each end of the array and a second set of electrodes positioned between the electrodes of the first set, wherein each electrode of the first set has a first diameter and each electrode of the second set has a second diameter.

6. The method of claim 5, wherein the first diameter is smaller than the second diameter.

7. The method of claim 1, wherein controlling the delivery further comprises:

increasing a delivery rate of energy to the target tissue volume by a first amount;

increasing the delivery rate of energy when a rate of increase of the temperature of the target tissue volume is equal to or less than a minimum rate;

decreasing the delivery rate of energy when the rate of increase of the temperature of the target tissue volume is equal to or greater than a maximum rate;

decreasing the delivery rate of energy when the temperature of the target tissue volume is greater than a maximum temperature;

increasing the delivery rate of energy to the target tissue volume by a second amount when the temperature of the target tissue volume is less than the maximum temperature; and terminating the delivery of energy to the target tissue volume when the elapsed time of the delivery exceeds a maximum time.

8. The method of claim 1, wherein controlling the delivery further comprises:

increasing a delivery rate of energy to the target tissue volume by a first amount;

maintaining the delivery rate of energy when the impedance of the target tissue is decreasing; and terminating the delivery of energy to the target tissue volume when the impedance of the target tissue exceeds a maximum impedance.

9. The method of claim 8, further comprising further increasing the delivery rate of energy to the target tissue volume by the first amount when the impedance of the target tissue is increasing or remaining approximately constant.

10. The method of claim 1, wherein controlling the delivery further comprises:

determining a first impedance of the target tissue volume;

delivering energy at a first rate to the target tissue volume;

monitoring the first impedance and delivering energy at a second rate when a decrease in the first impedance is less than a first threshold;

determining a second impedance of the target tissue volume in response to the decrease in the first impedance exceeding the first threshold;

monitoring the second impedance and delivering energy at a third rate when a decrease in the second impedance is less than a second threshold; and terminating the delivery of energy to the target tissue volume when the impedance of the target tissue exceeds a maximum impedance.

11. The method of claim 1, wherein controlling the delivery further comprises:

determining the impedance of the target tissue volume;

delivering the balanced energy to the target tissue volume at a first rate until the impedance stabilizes at a lower impedance; and delivering the balanced energy to the target tissue volume at a second rate until the impedance exceeds a threshold impedance.

12. The method of claim 1, wherein delivering the balanced energy further comprises supplying a first potential of RF energy to a first set of electrodes in the electrode array and a second potential of RF energy to a second set of electrodes in the electrode array.

13. The method of claim 1, further comprising:

incising the biological tissue in a vicinity of the plane of coagulated tissue; and resecting a portion of the biological tissue.

14. The method of claim 1, further comprising infusing a solution into the target tissue volume via at least one of the bipolar electrodes, wherein the solution is at least one of a hyper-tonic solution, a hypo-tonic solution, a contrast agent, a sclerotic agent, and a chemotherapy agent.

15. The method of claim 1, wherein at least one electrode of the electrode array further includes at least one of a temperature sensor, a thermocouple, an infusion component, and an optical tissue monitor.

16. The method of claim 1, wherein the balanced energy density includes uniform energy distribution and uniform current density.

17. The method of claim 1, wherein the bipolar electrodes of the electrode array form an alternating polarity series that includes at least one electrode of a positive polarity in series with at least one electrode of a negative polarity.

18. The method of claim 1, wherein the temperature of the target tissue volume includes at least one of a temperature of at least one area of the target tissue volume, a change in temperature of at least one area of the target tissue volume, and a rate of change of temperature of at least one area of the target tissue volume.

19. The method of claim 1, wherein the target tissue volume is a rectangular volume.

20. The method of claim 1, wherein controlling the delivery further comprises:

delivering a first amount of energy to the target tissue volume for a first period of time;

delivering a second amount of energy to the target tissue volume for a second period of time;

delivering a third amount of energy to the target tissue volume for a third period of time; and terminating the delivery of energy to the target tissue volume upon expiration of the third period of time.

21. The method of claim 20, wherein the first amount of energy is less than the second amount of energy and the third amount of energy is greater than the second amount of energy.

22. The method of claim 20, wherein the second and third periods of time are less than the first period of time.

23. The method of claim 20, wherein at least one of the first, second, and third amounts of energy are selected in response to the selected depth of deployment of at least one electrode.

24. The method of claim 20, wherein at least one of the first, second, and third periods of time are selected in response to the selected depth of deployment of at least one electrode.

25. The method of claim 1, wherein controlling the delivery further comprises:
    delivering at least one amount of energy to the target tissue volume for at least one period of time having at least one duration; and
    terminating the delivery of energy to the target tissue volume upon expiration of a pre-specified amount of time.

26. The method of claim 1, wherein controlling the delivery further comprises:
    delivering energy at one of a plurality of energy rates during at least one time period in response to the selected depth of deployment of at least one electrode; and
    terminating the delivery of energy to the target tissue volume upon expiration of a pre-specified amount of time.

27. A method for generating planes of coagulated tissue in biological tissue, comprising:
    configuring an electrode array that provides a balanced energy density in at least one target tissue volume using two or more pair of electrodes having a configuration that includes at least one of irregular spacing between one or more pairs of the electrodes and one or more electrode diameters;
    deploying each electrode of the electrode array at a selected depth in the target tissue volume using the configuration;
    determining an impedance of the target tissue volume;
    delivering the balanced energy to the target tissue volume at a first rate until the impedance stabilizes at a lower impedance; and
    generating at least one plane of coagulated tissue in the target tissue volume by delivering the balanced energy to the target tissue volume at a second rate until the impedance exceeds a threshold impedance.

28. The method of claim 27, wherein configuring further comprises varying spacing among the electrodes according to at least one of a total number of electrodes in the electrode array, the electrode diameters, and the selected deployment depth of each electrode in the target tissue volume.

29. The method of claim 27, wherein configuring further comprises spacing center-most electrodes of the electrode array at a larger distance relative to spacing of end-most electrodes of the electrode array.

30. The method of claim 27, wherein configuring the electrode array further comprises forming a linear electrode array that includes a first set of electrodes on each end of the array and a second set of electrodes positioned between the electrodes of the first set, wherein each electrode of the first set has a first diameter and each electrode of the second set has a second diameter.

31. A method for resecting a portion of biological tissue within a mammalian body, comprising:
    configuring an electrode array that provides a uniform energy density in at least one target tissue volume using two or more pair of electrodes that include at least one of irregular spacing between one or more pairs of the electrodes and one or more electrode diameters;
    deploying each electrode of the electrode array at a selected depth in the target tissue volume using the configuration;
    generating planes of coagulated tissue in the target tissue volume by delivering power to the target tissue volume from at least one power source via the electrodes and controlling the power delivery at two or more rates in response to at least one of elapsed time, a temperature of the target tissue volume, and an impedance of the target tissue volume;
    incising the biological tissue in a vicinity of the coagulated tissue; and
    resecting a portion of the biological tissue.

32. A method for performing thermal coagulation necrosis of biological tissue, comprising:
    configuring an electrode array that provides a balanced energy density in at least one target tissue volume using two or more pair of bipolar electrodes having a configuration that includes at least one of irregular spacing between one or more pairs of the electrodes and one or more electrode diameters;
    deploying each electrode of the electrode array at a selected depth in the target tissue volume using the configuration; and
    generating at least one plane of coagulated tissue by delivering the balanced energy to the target tissue volume from at least one power source via the electrodes by delivering energy at one of a plurality of energy rates during at least one time period in response to the selected depth of deployment of at least one electrode.

33. A method for performing thermal coagulation necrosis of biological tissue, comprising:
    configuring an electrode array that provides a balanced energy density in at least one target tissue volume using two or more pair of bipolar electrodes having a configuration that includes at least one of irregular spacing between one or more pairs of the electrodes and one or more electrode diameters, wherein the irregular spacing includes a first distance between electrodes of each pair of electrodes and a second distance between the pairs of electrodes;
    deploying each electrode of the electrode array at a selected depth in the target tissue volume using the configuration; and
    generating at least one plane of coagulated tissue by delivering the balanced energy to the target tissue volume from at least one power source via the electrodes and controlling the delivery in response to at least one of elapsed time of the delivery, a temperature of the target tissue volume, and an impedance of the target tissue volume.

34. The method of claim 33, wherein the first distance is equivalent for each pair of electrodes, and the second distance is equivalent between each pair of electrodes.

35. The method of claim 33, wherein controlling the delivery further comprises:

delivering energy at a first polarity to a first electrode of each pair of electrodes and delivering energy at a second polarity to a second electrode of each pair of electrodes for a first period of time; and delivering energy at the first polarity to the electrodes of a first pair of electrodes and delivering energy at the second polarity to the electrodes of a second pair of electrodes for a second period of time.

36. The method of claim 33, wherein controlling the delivery further comprises:

delivering energy at a first rate for a first period of time to each pair of electrodes; and delivering energy at a second rate for a second period of time to each pair of electrodes.

* * * * *